United States Patent
Anglese et al.

(10) Patent No.: US 9,877,777 B2
(45) Date of Patent: Jan. 30, 2018

(54) SURGICAL INSTRUMENT HAVING A BIPOLAR END EFFECTOR ASSEMBLY AND A DEPLOYABLE MONOPOLAR ASSEMBLY

(71) Applicant: COVIDIEN LP, Mansfield, MA (US)

(72) Inventors: Kurt J. Anglese, Lafayette, CO (US); Jason T. Sanders, Boulder, CO (US); Dylan R. Kingsley, Broomfield, CO (US); Gregory P. Hertrich, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 383 days.

(21) Appl. No.: 14/802,582

(22) Filed: Jul. 17, 2015

(65) Prior Publication Data
US 2016/0074653 A1 Mar. 17, 2016

Related U.S. Application Data

(60) Provisional application No. 62/051,416, filed on Sep. 17, 2014, provisional application No. 62/051,415, (Continued)

(51) Int. Cl.
*A61B 18/12* (2006.01)
*A61B 18/14* (2006.01)
(Continued)

(52) U.S. Cl.
CPC .......... *A61B 18/1445* (2013.01); *A61B 17/29* (2013.01); *A61B 18/1206* (2013.01);
(Continued)

(58) Field of Classification Search
CPC . A61B 17/29; A61B 18/1206; A61B 18/1445; A61B 18/1447; A61B 18/1482;
(Continued)

(56) References Cited

U.S. PATENT DOCUMENTS

| 4,005,714 A | 2/1977 | Hiltebrandt |
| D249,549 S | 9/1978 | Pike |

(Continued)

FOREIGN PATENT DOCUMENTS

| AU | 2011253698 A1 | 12/2011 |
| AU | 2013205789 A1 | 1/2014 |

(Continued)

OTHER PUBLICATIONS

W. Scott Helton, "LigaSure Vessel Sealing System: Revolutionary Hemostasis Product for General Surgery"; Sales/Product Literature 1999.

(Continued)

*Primary Examiner* — Daniel Fowler

(57) ABSTRACT

A deployment and retraction mechanism for deploying and retracting a deployable component of a surgical instrument includes a gear assembly, a slider, and one or more actuators. The slider is translatable between a proximal position, corresponding to a storage condition of the deployable component, and a distal position, corresponding to a use condition of the deployable component. The actuator(s) is coupled to the gear assembly and is movable from an un-actuated position to an actuated position. The gear assembly is configured such that a full actuation and subsequent release of the actuator(s) translates the slider from one of the proximal or distal positions to the other of the proximal or distal positions while a partial actuation and subsequent release of the actuator(s) translates the slider from one of the proximal or distal positions to an intermediate position and back to the one of the proximal or distal positions.

20 Claims, 19 Drawing Sheets

Related U.S. Application Data filed on Sep. 17, 2014, provisional application No. 62/051,412, filed on Sep. 17, 2014, provisional application No. 62/051,409, filed on Sep. 17, 2014.

(51) Int. Cl.
  *A61N 1/28* (2006.01)
  *A61B 18/00* (2006.01)
  *A61B 17/29* (2006.01)
  *A61B 34/35* (2016.01)

(52) U.S. Cl.
  CPC ...... *A61B 18/1447* (2013.01); *A61B 18/1482* (2013.01); *A61N 1/28* (2013.01); *A61B 34/35* (2016.02); *A61B 2017/2923* (2013.01); *A61B 2018/0091* (2013.01); *A61B 2018/00196* (2013.01); *A61B 2018/00398* (2013.01); *A61B 2018/00607* (2013.01); *A61B 2018/00922* (2013.01); *A61B 2018/00946* (2013.01); *A61B 2018/00958* (2013.01); *A61B 2018/126* (2013.01); *A61B 2018/1226* (2013.01); *A61B 2018/1253* (2013.01); *A61B 2018/1412* (2013.01); *A61B 2018/1422* (2013.01); *A61B 2018/1452* (2013.01); *A61B 2018/1475* (2013.01)

(58) Field of Classification Search
  CPC .. A61B 2017/2923; A61B 2018/00196; A61B 2018/00398; A61B 2018/00607; A61B 2018/0091; A61B 2018/00922; A61B 2018/00946; A61B 2018/00958; A61B 2018/1226; A61B 2018/1253; A61B 2018/126; A61B 2018/1412; A61B 2018/1422; A61B 2018/1452; A61B 2018/1457; A61B 34/35; A61N 1/25
  USPC .......................................... 74/52, 421 R, 435
  See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,026,379 A | 6/1991 | Yoon |
| D343,453 S | 1/1994 | Noda |
| 5,312,391 A | 5/1994 | Wilk |
| 5,318,589 A | 6/1994 | Lichtman |
| 5,324,254 A | 6/1994 | Phillips |
| D348,930 S | 7/1994 | Olson |
| D349,341 S | 8/1994 | Lichtman et al. |
| 5,342,359 A | 8/1994 | Rydell |
| 5,368,600 A | 11/1994 | Failla et al. |
| D354,564 S | 1/1995 | Medema |
| 5,401,274 A | 3/1995 | Kusunoki |
| D358,887 S | 5/1995 | Feinberg |
| 5,411,519 A | 5/1995 | Tovey et al. |
| 5,445,638 A | 8/1995 | Rydell et al. |
| 5,458,598 A | 10/1995 | Feinberg et al. |
| 5,501,654 A * | 3/1996 | Failla ................ A61B 17/0218 600/204 |
| 5,527,313 A | 6/1996 | Scott et al. |
| 5,556,397 A | 9/1996 | Long et al. |
| 5,611,813 A | 3/1997 | Lichtman |
| D384,413 S | 9/1997 | Zlock et al. |
| H1745 H | 4/1998 | Paraschac |
| 5,735,873 A | 4/1998 | MacLean |
| 5,792,164 A | 8/1998 | Lakatos et al. |
| 5,807,393 A | 9/1998 | Williamson, IV et al. |
| D402,028 S | 12/1998 | Grimm et al. |
| D408,018 S | 4/1999 | McNaughton |
| 5,893,863 A | 4/1999 | Yoon |
| 5,919,202 A | 7/1999 | Yoon |
| D416,089 S | 11/1999 | Barton et al. |
| 6,004,319 A | 12/1999 | Goble et al. |
| D424,694 S | 5/2000 | Tetzlaff et al. |
| D425,201 S | 5/2000 | Tetzlaff et al. |
| 6,113,596 A | 9/2000 | Hooven et al. |
| H1904 H | 10/2000 | Yates et al. |
| 6,156,009 A | 12/2000 | Grabek |
| 6,190,386 B1 | 2/2001 | Rydell |
| 6,270,497 B1 | 8/2001 | Sekino et al. |
| D449,886 S | 10/2001 | Tetzlaff et al. |
| 6,299,625 B1 | 10/2001 | Bacher |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,387,094 B1 | 5/2002 | Eitenmuller |
| H2037 H | 7/2002 | Yates et al. |
| D465,281 S | 11/2002 | Lang |
| D466,209 S | 11/2002 | Bon |
| 6,551,313 B1 | 4/2003 | Levin |
| 6,558,385 B1 | 5/2003 | McClurken et al. |
| 6,679,882 B1 | 1/2004 | Kornerup |
| D493,888 S | 8/2004 | Reschke |
| D496,997 S | 10/2004 | Dycus et al. |
| 6,808,525 B2 | 10/2004 | Latterell et al. |
| D499,181 S | 11/2004 | Dycus et al. |
| 6,837,888 B2 | 1/2005 | Ciarrocca et al. |
| D502,994 S | 3/2005 | Blake, III |
| D509,297 S | 9/2005 | Wells |
| 6,942,662 B2 | 9/2005 | Goble et al. |
| 7,033,356 B2 | 4/2006 | Latterell et al. |
| 7,063,699 B2 | 6/2006 | Hess et al. |
| D525,361 S | 7/2006 | Hushka |
| D531,311 S | 10/2006 | Guerra et al. |
| 7,128,254 B2 | 10/2006 | Shelton, IV et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| 7,208,005 B2 | 4/2007 | Frecker et al. |
| D541,611 S | 5/2007 | Aglassinger |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| 7,402,162 B2 | 7/2008 | Ouchi |
| D575,395 S | 8/2008 | Hushka |
| D575,401 S | 8/2008 | Hixson et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,481,810 B2 | 1/2009 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,577 B2 | 7/2010 | Nobis et al. |
| D621,503 S | 8/2010 | Otten et al. |
| 7,789,878 B2 | 9/2010 | Dumbauld et al. |
| 7,815,636 B2 | 10/2010 | Ortiz |
| 7,819,299 B2 | 10/2010 | Shelton, IV et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,879,035 B2 | 2/2011 | Garrison et al. |
| D649,249 S | 11/2011 | Guerra |

(56) References Cited

U.S. PATENT DOCUMENTS

| | | |
|---|---|---|
| D649,643 S | 11/2011 | Allen, IV et al. |
| D661,394 S | 6/2012 | Romero et al. |
| 8,257,352 B2 | 9/2012 | Lawes et al. |
| 8,333,765 B2 | 12/2012 | Johnson et al. |
| 8,353,437 B2 | 1/2013 | Boudreaux |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| RE44,834 E | 4/2014 | Dumbauld et al. |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Homer et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chemova et al. |
| 9,113,934 B2 | 8/2015 | Chemov et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0187547 A1 | 8/2005 | Sugi |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0110958 A1 | 5/2008 | McKenna et al. |
| 2008/0215050 A1 | 9/2008 | Bakos |
| 2008/0243120 A1 | 10/2008 | Lawes et al. |
| 2008/0314954 A1 | 12/2008 | Boudreaux |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0004209 A1 | 1/2011 | Lawes et al. |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0184988 A1 | 7/2012 | Twomey et al. |
| 2012/0209263 A1 | 8/2012 | Sharp et al. |
| 2012/0239034 A1 | 9/2012 | Homer et al. |
| 2012/0259331 A1 | 10/2012 | Garrison |
| 2012/0265241 A1 | 10/2012 | Hart et al. |
| 2012/0296205 A1 | 11/2012 | Chemov et al. |
| 2012/0296238 A1 | 11/2012 | Chemov et al. |
| 2012/0296239 A1 | 11/2012 | Chemov et al. |
| 2012/0296323 A1 | 11/2012 | Chemov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chemov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Homer et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |

(56) References Cited

U.S. PATENT DOCUMENTS

| | | |
|---|---|---|
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0135763 A1 | 5/2014 | Kappus et al. |
| 2014/0276797 A1 | 9/2014 | Batchelor et al. |

FOREIGN PATENT DOCUMENTS

| | | |
|---|---|---|
| CN | 21299462 | 9/2009 |
| CN | 201299462 | 9/2009 |
| DE | 03612646 A1 | 4/1957 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| EP | 2679176 A1 | 1/2014 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 10-019884 | 1/1998 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2001-520543 A | 10/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 98/46150 A1 | 10/1998 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 02/45589 A2 | 6/2002 |
| WO | 2005/110264 A2 | 11/2005 |
| WO | 2006021269 A1 | 3/2006 |
| WO | 05110264 A3 | 4/2006 |
| WO | 2007118608 A1 | 10/2007 |
| WO | 08/040483 A1 | 4/2008 |
| WO | 2011/018154 A1 | 2/2011 |

OTHER PUBLICATIONS

Levy et al., "Update on Hysterectomy—New Technologies and Techniques" OBG Management, Feb. 2003.
European Search Report issued in corresponding application No. 15178245.5 dated Feb. 4, 2016.
Australian office action issued in corresponding application No. 2015221567 dated Nov. 9, 2016.
Japanese office action issued in corresponding Japanese application No. 2016-209496 dated Aug. 9, 2017 (6 pages).
U.S. Appl. No. 08/926,869, James G. Chandler.
U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
Michael Choti, "Abdominoperineal Resection with the LigaSure Vessel Sealing System and LigaSure Atlas 20 cm Open Instrument"; Innovations That Work, Jun. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery", 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.

(56) References Cited

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room", 2001.

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex", 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

\* cited by examiner

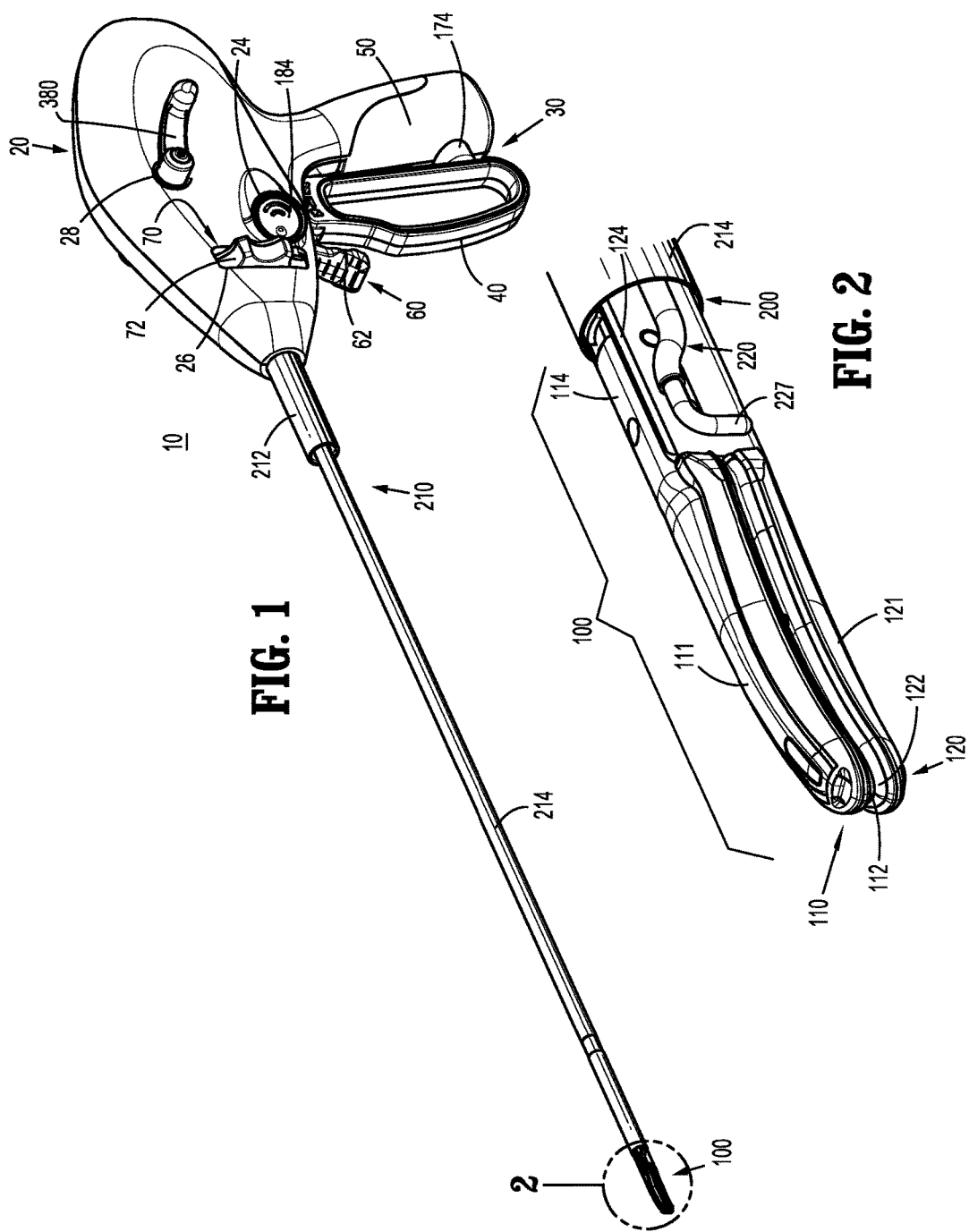

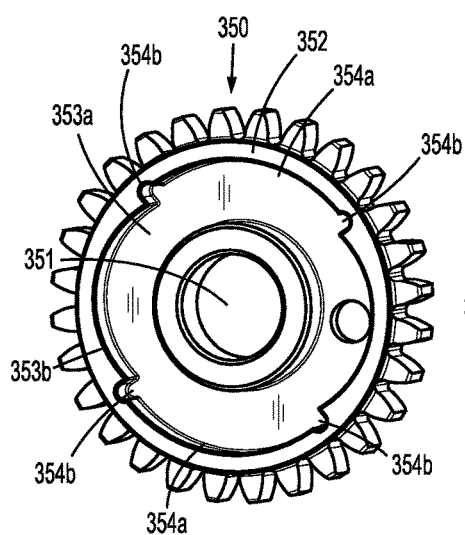
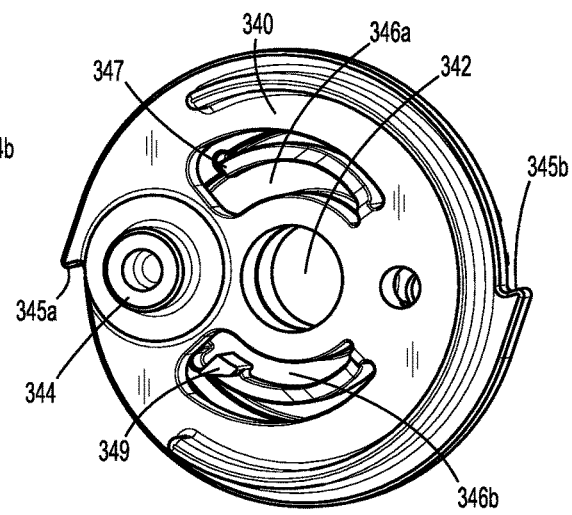
FIG. 18  FIG. 19
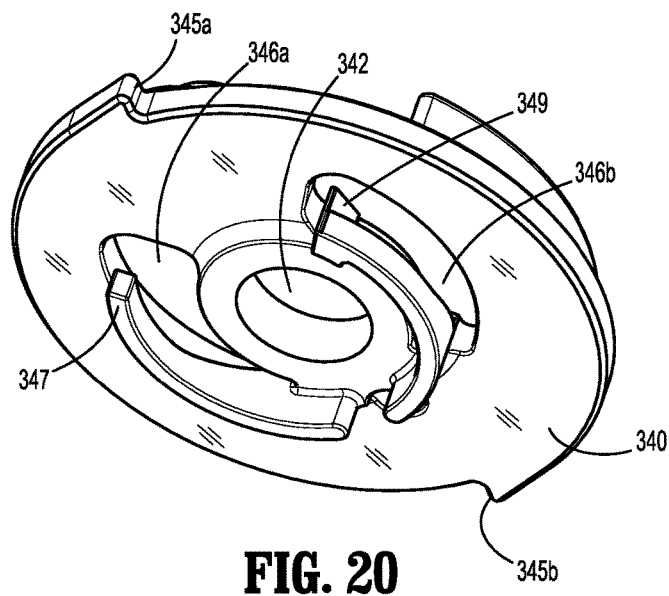
FIG. 20

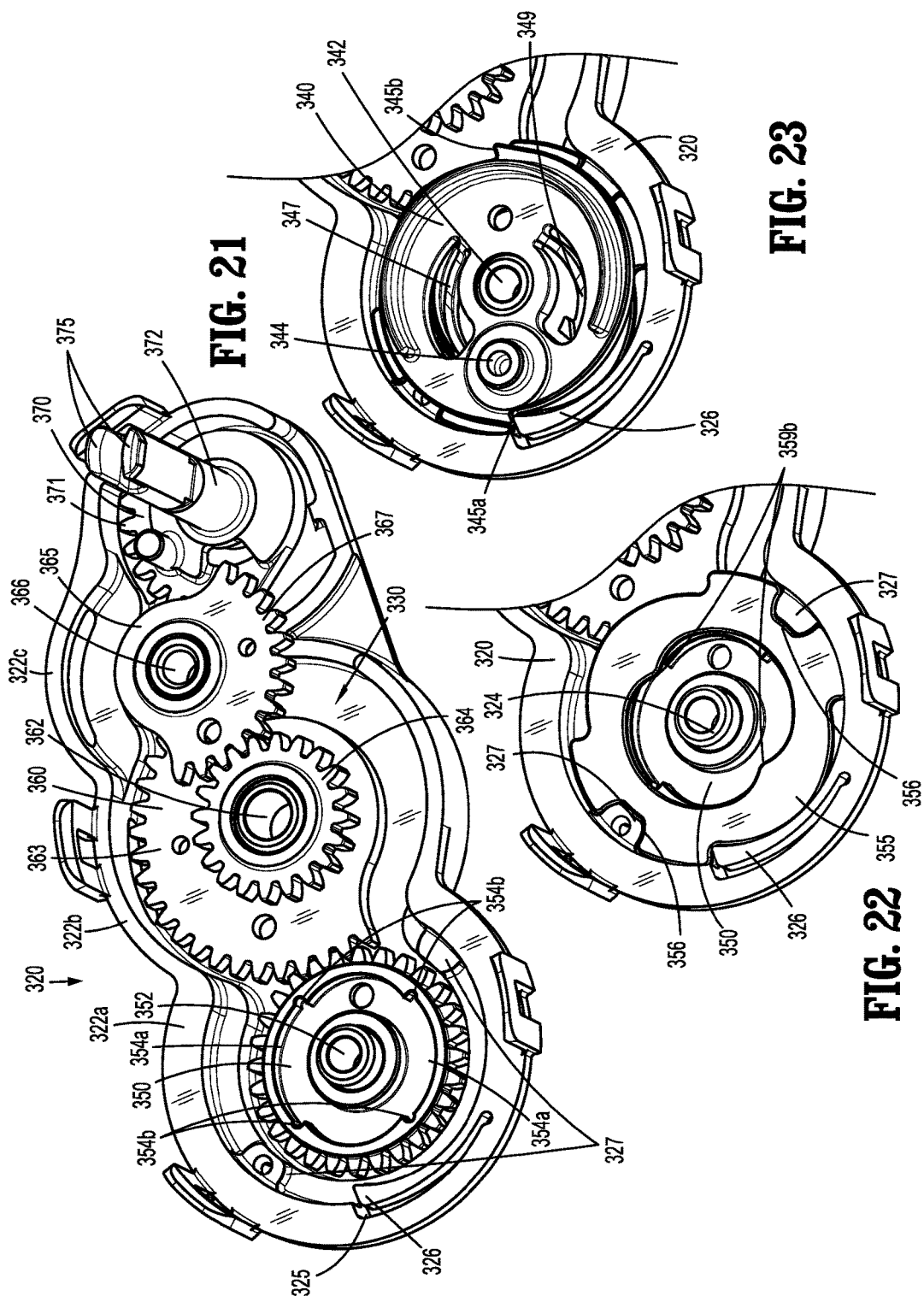

SURGICAL INSTRUMENT HAVING A BIPOLAR END EFFECTOR ASSEMBLY AND A DEPLOYABLE MONOPOLAR ASSEMBLY

CROSS REFERENCES TO RELATED APPLICATION

This application claims the benefit of, and priority to, U.S. Provisional Patent Application Nos. 62/051,416, 62/051,415, 62/051,412, and 62/051,409 all of which were filed on Sep. 17, 2014. This application is related to U.S. patent application Ser. Nos. 14/802,654, 14/802,687, and 14/802,726 all of which were filed on Jul. 17, 2015. The entire contents of each of the above applications are hereby incorporated herein by reference.

BACKGROUND

Technical Field

The present disclosure relates to surgical instruments and, more particularly, to a multi-function surgical instrument including a bipolar end effector assembly and a deployable monopolar assembly.

Background of Related Art

Bipolar surgical instruments typically include two generally opposing electrodes charged to different electric potentials to selectively apply energy to tissue. Bipolar electrosurgical forceps, for example, utilize both mechanical clamping action and electrical energy to effect hemostasis by heating tissue to coagulate and/or cauterize tissue. Certain surgical procedures require more than simply coagulating and/or cauterizing tissue and rely on the unique combination of clamping pressure, precise electrosurgical energy control, and gap distance (i.e., distance between opposing jaw members when closed about tissue) to "seal" tissue. Once tissue is sealed or otherwise treated, e.g., cauterized, coagulated, desiccated, etc., it is often desirable to cut the treated tissue. Accordingly, many forceps have been designed which incorporate a knife that effectively severs the tissue after tissue treatment.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be treated. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

As can be appreciated, as additional functional components are added to a surgical instrument, additional deployment structures or deployment structures capable of actuating more than one component are required. However, multiple deployment structures and/or combined deployment structures may be limited by spatial constraints within the housing of the surgical instrument, functional constraints of the components (e.g., where a combined deployment structure imparts additional force requirements for deploying one or more of the components coupled thereto), and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a deployment and retraction mechanism for selectively deploying and retracting a deployable component of a surgical instrument. The deployment and retraction mechanism includes a gear box housing a gear assembly, a slider operably coupled to an output of the gear assembly, and one or more actuators operably coupled to an input of the gear assembly. The slider is configured to engage a deployable component of a surgical instrument and is selectively translatable relative to the gear box between a proximal position, corresponding to a storage condition of the deployable component, and a distal position, corresponding to a use condition of the deployable component. The actuator(s) is movable from an un-actuated position to an actuated position. A full actuation of the actuator(s) is defined as movement of the actuator(s) from the un-actuated position to the actuated position. The gear assembly is configured such that, upon a full actuation and subsequent release of the actuator(s), the slider is translated from one of the proximal or distal positions to the other of the proximal or distal positions, and the actuator(s) is returned from the actuated position to the un-actuated position independent of the slider. The gear assembly is further configured such that, upon a partial actuation and subsequent release of the actuator(s), the slider is translated from one of the proximal or distal positions to an intermediate position between the proximal and distal positions and back to the one of the proximal or distal positions, and the actuator(s) is returned from a partially-actuated position between the un-actuated position and the actuated position to the un-actuated position in connection with the translation of the slider back to the one of the proximal or distal position.

In an aspect of the present disclosure, the gear box defines a longitudinal slot having a proximal end and a distal end. In such aspects, the slider is slidable between a proximal end of the longitudinal slot, corresponding to the proximal position of the slider, and a distal end of the longitudinal slot, corresponding to the distal position of the slider. Further, the slider may be operably engaged within a track extending along opposed sides of the longitudinal slot.

In another aspect of the present disclosure, the actuator(s) is biased towards the un-actuated position.

In still another aspect of the present disclosure, the gear assembly includes a ring gear disposed within the gear box and positioned to surround the longitudinal slot and a planet gear coupled to the input of the gear assembly and operably engaged with the ring gear to orbit within the ring gear. The planet gear includes an off-center pin rotatably supporting the slider thereon. The planet gear and the ring gear are configured such that a one-half orbit of the planet gear within the ring gear translates the slider from one of the proximal or distal positions to the other of the proximal or distal positions.

In yet another aspect of the present disclosure, a full actuation of the actuator(s) urges the planet gear to orbit through a one-half orbit and wherein a partial actuation of the actuator(s) urges the planet gear to orbit less than a one-half orbit.

In still yet another aspect of the present disclosure, the gear assembly further includes a carrier member defining an off-center pivot received within a central aperture defined within the planet gear to operably couple the planet gear and the carrier member such that rotation of the carrier member orbits the planet gear within the ring gear.

In another aspect of the present disclosure, the gear assembly further includes a ratchet gear releasably engagable with the carrier member.

In yet another aspect of the present disclosure, the actuator(s) is operably coupled to the ratchet gear such that actuation of the actuator(s) effects rotation of the ratchet gear to thereby rotate the carrier member when the ratchet gear is engaged with the carrier member.

In still another aspect of the present disclosure, the gear assembly further includes a disengagement plate disposed between the ratchet gear and the carrier member. The disengagement plate is configured to selectively disengage the ratchet gear from the carrier member upon a full actuation of the actuator(s).

In still yet another aspect of the present disclosure, the ratchet gear remains engaged with the carrier member upon a partial actuation of the actuator(s).

A surgical instrument provided in accordance with the present disclosure includes a housing having a shaft extending distally therefrom, an end effector assembly disposed at a distal end of the shaft, a deployable assembly selectively movable relative to the end effector assembly between a storage condition and a use condition, and a deployment and retraction mechanism for selectively deploying and retracting the deployable assembly. The deployment and retraction mechanism may include any of the features of any or all of the aspects detailed above.

In an aspect of the present disclosure, the deployable assembly includes an elongated insulative sheath slidably disposed about the shaft and an energizable member slidably disposed within the shaft. Further, in the storage condition, the elongated insulative sheath and the energizable member may be positioned proximally of the end effector assembly. In the use condition, the elongated insulative sheath may extend about the end effector assembly and the energizable member may extend distally from the end effector assembly.

BRIEF DESCRIPTION OF THE DRAWINGS

Various aspects of the present disclosure are described herein with reference to the drawings wherein like reference numerals identify similar or identical elements:

FIG. 1 is a front, perspective view of an endoscopic surgical instrument provided in accordance with the present disclosure with the monopolar assembly thereof disposed in a storage condition;

FIG. 2 is an enlarged, perspective view of the area of detail indicated as "2" in FIG. 1;

FIG. 18 is a side, perspective view of a ratchet gear of the deployment and retraction mechanism of FIG. 7;

FIG. 19 is a perspective view of the carrier member of FIG. 17 operably positioned relative to the ratchet gear of FIG. 18;

FIG. 20 is a perspective view of the carrier member of FIG. 17;

FIG. 21 is a side, perspective view of the deployment and retraction mechanism of FIG. 7 with portions removed to illustrate the operable engagement of internal components thereof;

FIG. 22 is side, perspective view of the proximal end of the deployment and retraction mechanism as illustrated in FIG. 21, further including a disengagement plate;

FIG. 23 is a side, perspective view of the proximal end of the deployment and retraction mechanism as illustrated in FIG. 22, further including the carrier member;

DETAILED DESCRIPTION

Figure 3:
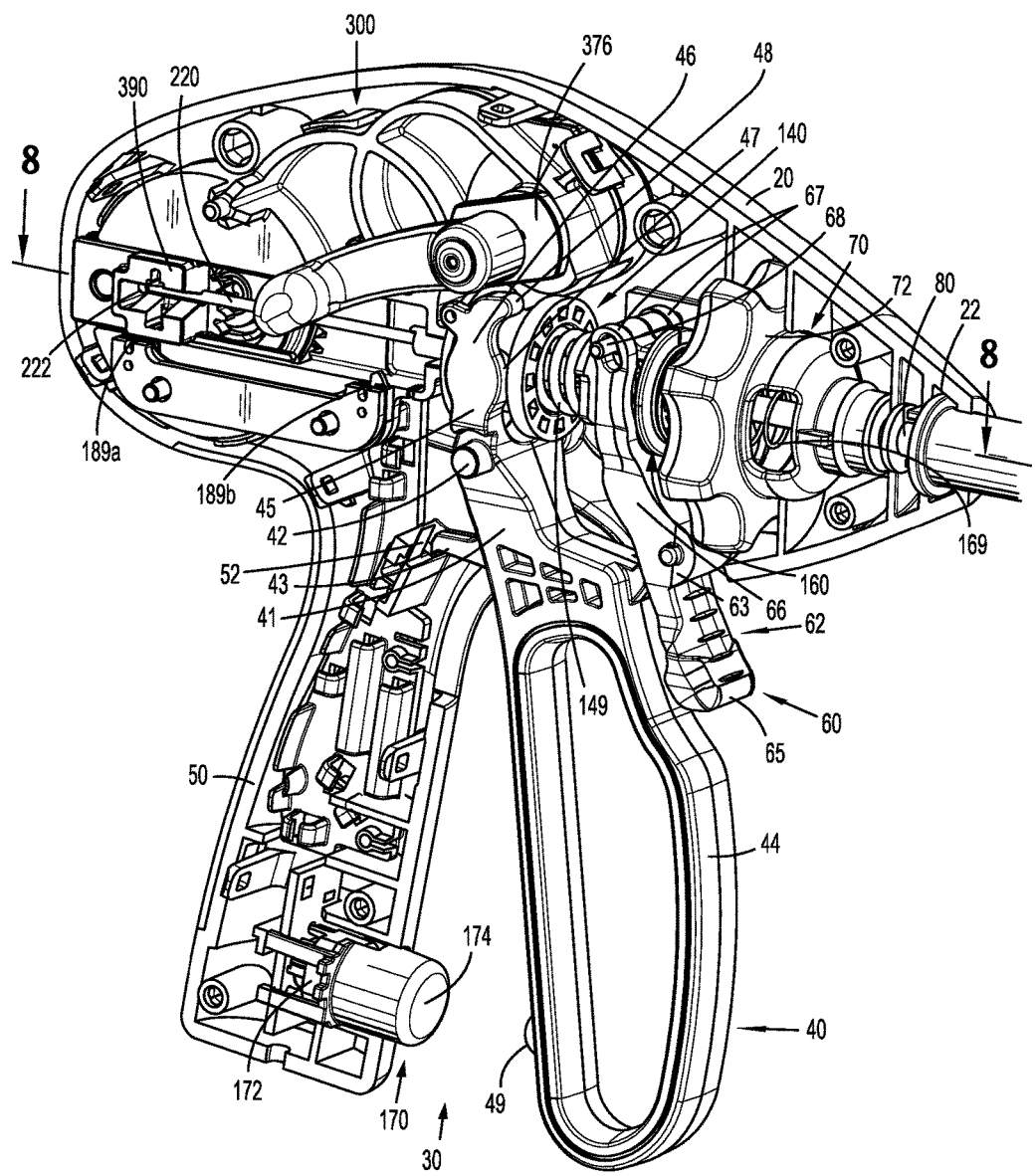
FIG. 3 is a front, perspective view from a first side of the proximal end of the surgical instrument of FIG. 1 with portions removed to illustrate the internal working components thereof.

Referring generally to FIGS. 1-6, an endoscopic surgical instrument provided in accordance with the present disclosure is shown generally identified by reference numeral 10. Instrument 10, as described below, is configured to operate in both a bipolar mode, e.g., for grasping, treating, and/or mechanically dissecting tissue, and a monopolar mode, e.g., for treating and/or electrically/electromechanically dissecting tissue. Although the present disclosure is shown and described with respect to instrument 10, the aspects and features of the present disclosure are equally applicable for use with any suitable surgical instrument or portion(s) thereof for selectively actuating, moving, and/or deploying one or more assemblies and/or components of the surgical instrument, for example, to transition between a bipolar mode of operation and a monopolar mode of operation. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1-6, instrument 10 generally includes a housing 20, a handle assembly 30, a trigger assembly 60, a rotating assembly 70, a shaft 80, an end effector assembly 100, a drive assembly 140, a knife assembly 160, bipolar and monopolar activation assemblies 170, 180, respectively, a monopolar assembly 200, and a deployment and retraction mechanism 300. As detailed below, shaft 80 extends distally from housing 20 and supports end effector assembly 100 at a distal end thereof, drive assembly 140 operably couples handle assembly 30 with end effector assembly 100 to enable selective manipulation of jaw members 110, 120 of end effector assembly 100, knife assembly 160 is operably coupled with trigger assembly 60 to enable selective translation of a knife 164 of knife assembly 160 relative to end effector assembly 100, and deployment and retraction mechanism 300 is operably coupled with monopolar assembly 200 to enable selective deployment and retraction of monopolar assembly 200. Rotating assembly 70 enables selective rotation of end effector assembly 100 and monopolar assembly 200 relative to shaft 80, while bipolar and monopolar activation assemblies 170, 180 enable the appropriate energy to be selectively delivered to end effector assembly 100 and monopolar assembly 200, respectively.

Instrument 10 may also include an electrosurgical cable (not shown) that connects instrument 10 to a generator (not shown) or other suitable power source, although instrument 10 may alternatively be configured as a battery-powered instrument. The electrosurgical cable (not shown) includes wires (not shown) extending therethrough that have sufficient length to extend through housing 20 and/or shaft 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of the electrosurgical cable (not shown) extends through housing 20 and/or shaft 80 in order to provide energy to monopolar assembly 200, e.g., upon activation of either of the monopolar activation switches 182 of monopolar activation assembly 180 in the monopolar mode of operation. As can be appreciated, additional wires (not shown) are provided to electrically couple the various inter-operable electrical components of instrument 10, as detailed below.

Figure 4:
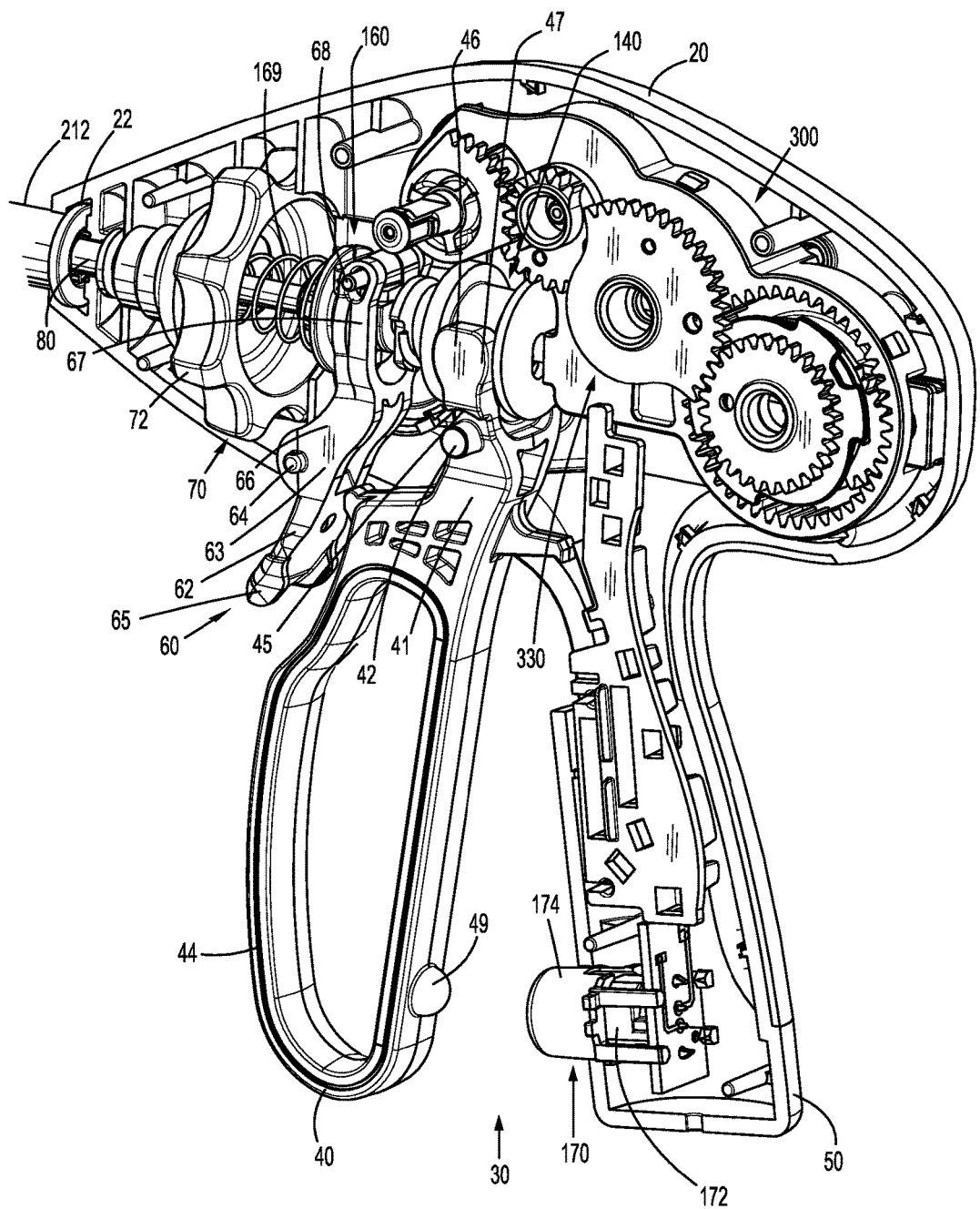
FIG. 4 is a rear, perspective view from a second side of the proximal end of the surgical instrument of FIG. 1 with portions removed to illustrate the internal working components thereof.
Figure 5:
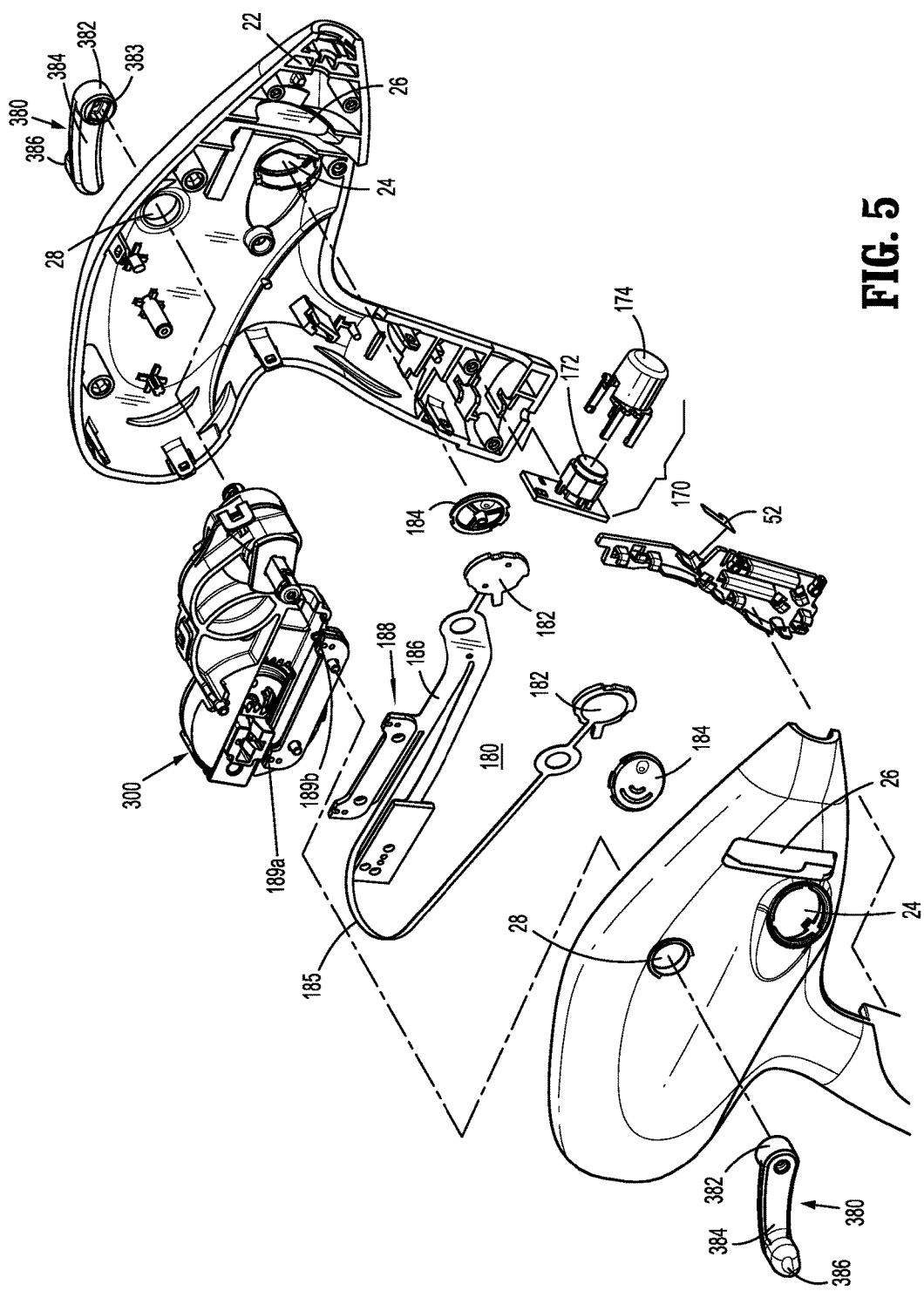
FIG. 5 is an exploded, perspective view of the proximal end of the surgical instrument of FIG. 1 with portions removed.

With reference to FIG. 2, end effector assembly 100 is attached at the distal end of shaft 80 (FIG. 6) and includes opposing jaw members 110, 120 pivotably coupled to one another. Each of the jaw members 110, 120 includes a jaw body 111, 121 supporting the respective electrically-conductive surface 112, 122, and a respective proximally-extending jaw flange 114, 124. Jaw bodies 111, 121 define a curved configuration, although other configurations are also contemplated. Flanges 114, 124 are pivotably coupled to one another to permit movement of jaw members 110, 120 relative to one another between a spaced-apart position and an approximated position for grasping tissue between surfaces 112, 122. One or both of surfaces 112, 122 are adapted to connect to the source of energy (not shown), e.g., via one or more wires (not shown), and are configured to conduct energy through tissue grasped therebetween to treat tissue, e.g., cauterize, coagulate/desiccate, and/or seal tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating tissue. Referring additionally to FIGS. 3-5, bipolar activation switch 172 of bipolar activation assembly 170 is operably coupled between the source of energy (not shown) and surfaces 112, 122 via one or more wires (not shown), thus allowing the user to selectively apply energy to surfaces 112, 122 of jaw members 110, 120, respectively, of end effector assembly 100 during a bipolar mode of operation.

Figure 6:
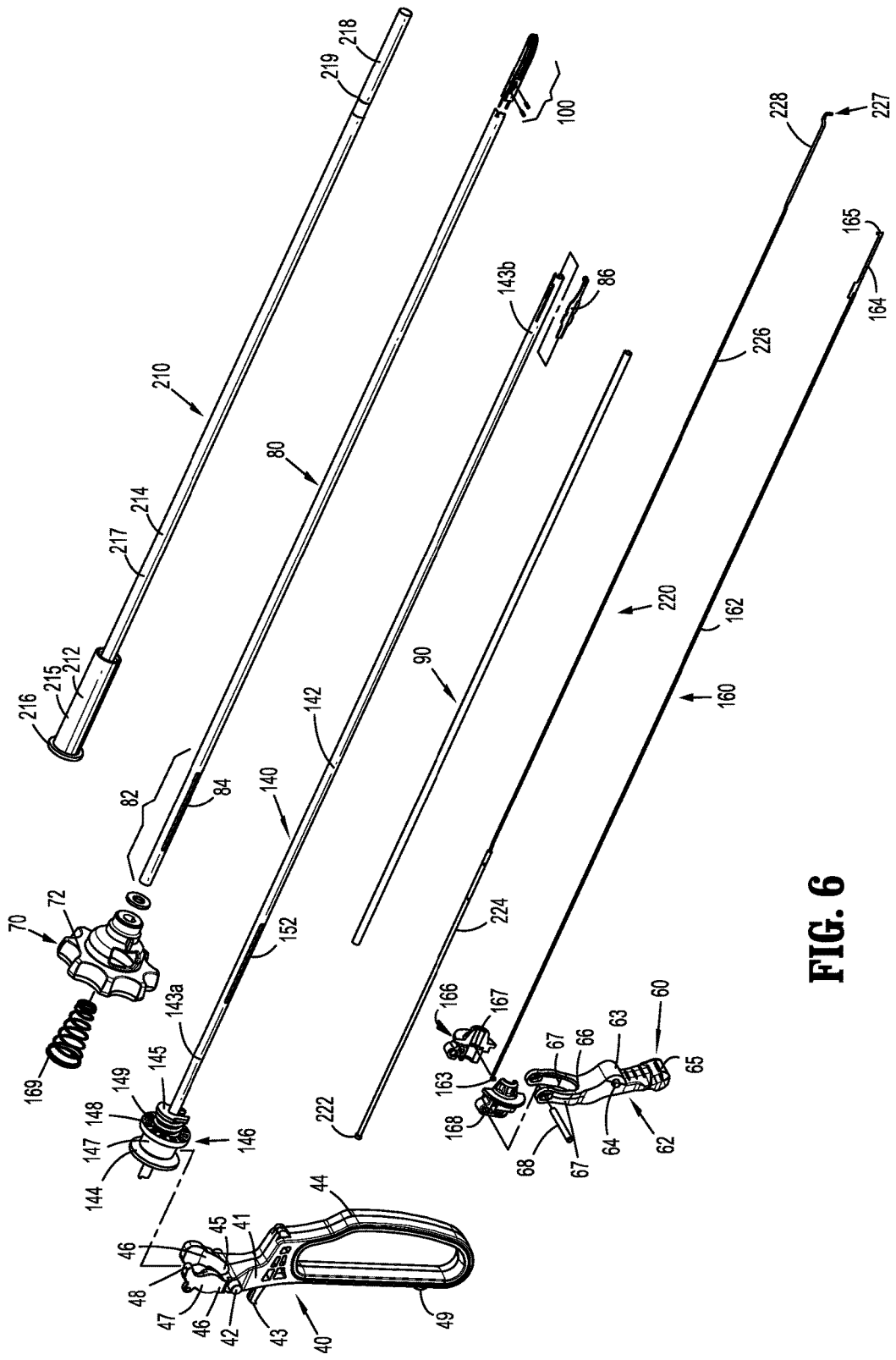
FIG. 6 is an exploded, perspective view of various operable assemblies of the surgical instrument of FIG. 1.

End effector assembly 100 is designed as a unilateral assembly, i.e., where jaw member 120 is fixed relative to shaft 80 (FIG. 6) and jaw member 110 is movable relative to shaft 80 (FIG. 6) and fixed jaw member 120. However, end effector assembly 100 may alternatively be configured as a bilateral assembly, i.e., where both jaw member 110 and jaw member 120 are movable relative to one another and to shaft 80 (FIG. 6). Further, in some embodiments, a longitudinally-extending knife channel (not shown) may be defined within one or both of jaw members 110, 120 to permit reciprocation of knife 164 (FIG. 6) therethrough, e.g., upon actuation of a trigger 62 of trigger assembly 60, to cut tissue grasped between jaw members 110, 120. Jaw members 110, 120 of end effector assembly 100 may otherwise be configured similar to those of the end effector assembly detailed in U.S. patent application Ser. No. 14/196,066, filed on Mar. 4, 2014, the entire contents of which are hereby incorporated herein by reference.

Referring to FIGS. 3-6, handle assembly 30 includes movable handle 40 and a fixed handle 50. Fixed handle 50 is integrally associated with housing 20 and movable handle 40 is movable relative to fixed handle 50 between an initial position, wherein movable handle 40 is spaced-apart from fixed handle 50, and a compressed position, wherein movable handle 40 is compressed towards fixed handle 50. More specifically, an intermediate portion 41 of movable handle 40 is pivotably coupled within housing 20 on either side of housing 20 via a split pivot 42. Intermediate portion 41 of movable handle 40 includes a tooth 43 extending proximally from intermediate portion 41, the importance of which is detailed below. A grasping portion 44 of movable handle 40 extends from split pivot 42 in a first direction, ultimately exiting housing 20 to facilitate grasping and manipulation of movable handle 40 from the exterior of housing 20. A bifurcated portion 45 of movable handle 40 extends from split pivot 42 in a second, opposite direction further into housing 20. Bifurcated portion 45 of movable handle 40 includes a pair of spaced-apart flanges 46 each including an enlarged area 47. One of flanges 46 also include a finger 48 extending from the free end thereof, the importance of which is detailed below.

Figure 8:
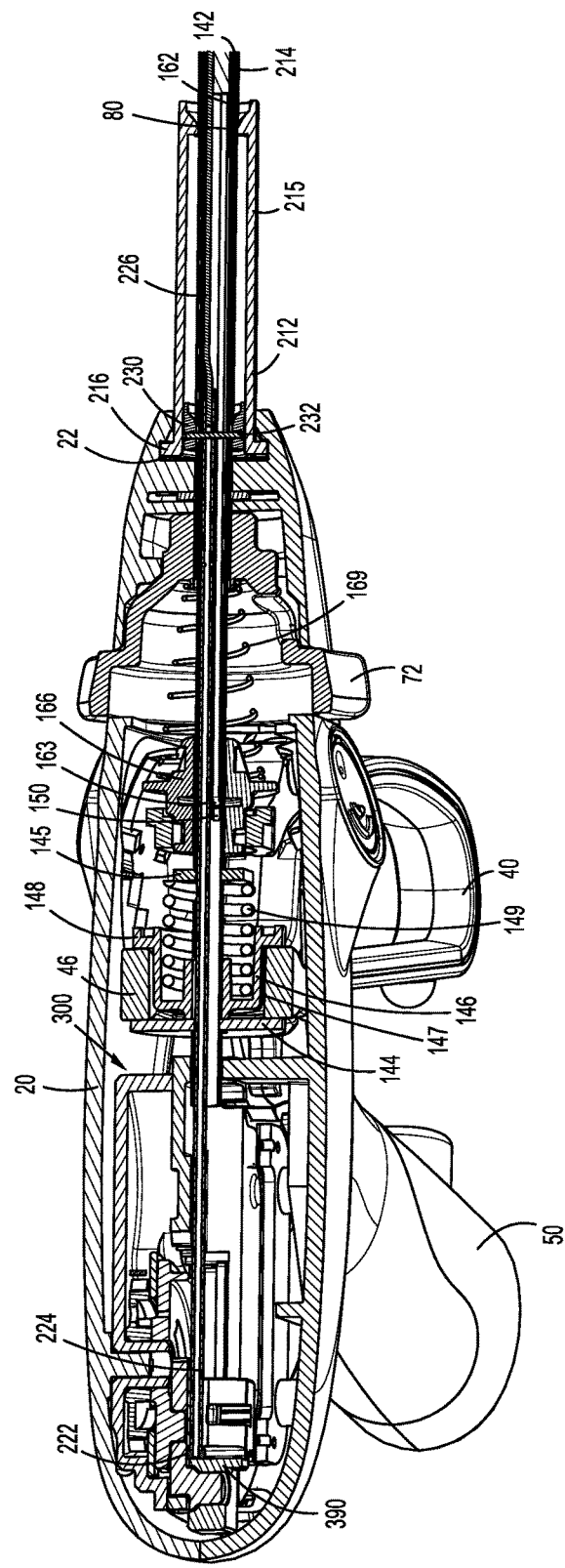
FIG. 8 is a cross-sectional view taken along section line "8-8" of FIG. 3.

Drive assembly 140 includes a drive bar 142 that is slidably disposed within shaft 80 and configured to operably couple movable handle 40 with end effector assembly 100. More specifically, a proximal end 143a of drive bar 142 is operably coupled to movable handle 40 while a distal end 143b of drive bar is operably coupled to jaw members 110, 120. A proximal collar 144 is engaged about drive bar 142 towards the proximal end 143a thereof and a clip 145 is engaged about drive bar 142 towards proximal end 143a thereof but distally-spaced from proximal collar 144. A mandrel 146 having a proximal sleeve 147 and a distal washer 148 is slidably disposed about drive bar 142 between proximal collar 144 and clip 145. A biasing member 149 is disposed about drive bar 142 between distal washer 148 of mandrel 146 and clip 145. Spaced-apart flanges 46 of movable handle 40 are disposed on either side of proximal sleeve 147 of mandrel 146 with enlarged areas 47 of spaced-apart flanges 46 disposed longitudinally between proximal collar 144 and distal washer 148. Drive bar 142 further includes an elongated cut-out 150 (FIG. 8) and a pair of opposed longitudinal slots 152 defined therethrough, the importance of which are detailed below.

As noted above, bipolar activation switch 172 of bipolar activation assembly 170 is provided to selectively supply energy to surfaces 112, 122 (FIG. 2) of jaw members 110, 120, respectively, of end effector assembly 100. Bipolar activation switch 172 is disposed within fixed handle 50 adjacent a depressible button 174 that is operably coupled to and extends from fixed handle 50. Upon sufficient compression of movable handle 40 relative to fixed handle 50, a button activation post 49 extending from movable handle 40 is urged into contact with depressible button 174 so as to depress depressible button 174 into fixed handle 50 to activate bipolar activation switch 172. Bipolar activation switch 172 is disposed in electrical communication with the source of energy (not shown) and surfaces 112, 122 (FIG. 2) of jaw members 110, 120 via one or more wires (not shown).

In use, upon compression of movable handle 40 towards fixed handle 50, grasping portion 44 of movable handle 40 is pivoted about split pivot 42 in a generally proximal direction while bifurcated portion 45 of movable handle 40 is pivoted about split pivot 42 in a generally distal direction. Such distal movement of bifurcated portion 45 of movable handle 40 urges enlarged areas 47 of spaced-apart flanges 46 distally into contact with distal washer 148 to thereby urge distal mandrel 146 to slide distally about drive bar 142. Distal sliding of mandrel 146 about drive bar 142 compresses biasing member 149 between distal washer 148 of mandrel 146 and clip 145 until sufficient potential energy is built up to urge clip 145 distally, thereby translating drive bar 142 distally through shaft 80 and relative to end effector assembly 100 to pivot jaw member 110 relative to jaw member 120 from the spaced-apart position to the approximated position to grasp tissue therebetween.

As movable handle 40 is compressed towards fixed handle 50, tooth 43 of intermediate portion 41 of movable handle 40 engages a clicker tab 52 supported within fixed handle 50 to generate a tactile and/or an audible response. Clicker tab 52 may be constructed of a plastic film, sheet metal, or any suitable material configured to generate a "clicking" sound as clicker tab 52 is engaged and disengaged by tooth 43. The response generated by clicker tab 52 indicates to the user that jaw members 110, 120 are sufficiently approximated so as to grasp tissue therebetween and that further compression of movable handle 40 toward fixed handle 50 will cause button activation post 49 to contact and depress depressible button 174 to activate bipolar activation switch 172. Thus, upon further compression of movable handle 40, bipolar activation switch 172 is activated to initiate the delivery of energy to surfaces 112, 122 (FIG. 2) of jaw members 110, 120 to treat tissue grasped therebetween.

Once tissue has been treated, movable handle 40 is released or returned to its initial position. Upon return of movable handle 40 to the initial position, spaced-apart flanges 46 of bifurcated portion 45 of movable handle 40 are returned proximally to thereby return mandrel 146 and drive bar 142 proximally such that jaw member 110 is pivoted relative to jaw member 120 back to the spaced-apart position. Movable handle 40 may further include a biasing member (not shown) for biasing movable handle 40 towards the initial position such that, upon release of movable handle 40, movable handle 40 is returned to its initial position and, accordingly, jaw member 110 is returned to the spaced-apart position relative to jaw member 120.

Referring still to FIGS. 3-6, trigger 62 of trigger assembly 60 is selectively actuatable relative to housing 20 from an un-actuated position to an actuated position. More specifically, trigger 62 includes an intermediate portion 63 having a split pivot 64 about which trigger 62 is pivotably coupled to housing 20 on either side of housing 20. A toggle portion 65 of trigger 62 extends from split pivot 64 in a first direction, ultimately exiting housing 20 to facilitate manipulation of trigger 62 from the exterior of housing 20. A bifurcated portion 66 of trigger 62 extends from split pivot 64 in a second, opposite direction further into housing 20. Bifurcated portion 66 of trigger 62 includes a pair of spaced-apart arms 67 interconnected via a transverse pin 68.

Knife assembly 160 is operably coupled to trigger 62 such that actuation of trigger 62 from the un-actuated position to the actuated position translates knife 164 of knife assembly 160 from a retracted position, wherein knife 164 is disposed within shaft 80 proximally of jaw members 110, 120, to an extended position, wherein knife 164 extends at least partially between jaw members 110, 120 and through the knife channel(s) (not shown) thereof to cut tissue grasped between jaw members 110, 120. Knife assembly 160 includes a knife bar 162 that is slidably disposed within drive bar 142, knife 164, and a knife collar 166. Knife 164 is engaged to and extends distally from knife bar 162. Knife 164 defines a sharpened distal cutting edge 165 to facilitate cutting tissue, although other configurations are also contemplated. Knife collar 166 is slidably disposed about drive bar 142 of drive assembly 140. A proximal foot 163 of knife bar 162 extends through elongated cut-out 150 (FIG. 8) defined through drive bar 142 and is received within a corresponding slot 167 defined within knife collar 166 to engage knife collar 166 about the proximal end of knife bar 162. Knife collar 166 further defines a transverse aperture 168 configured to receive transverse pin 68 of trigger assembly 60 to operably couple trigger assembly 60 and knife assembly 160 with one another.

In use, upon actuation of trigger 62 from the un-actuated position to the actuated position, toggle portion 65 of trigger is pivoted about split pivot 64 in a generally proximal direction while bifurcated portion 66 is pivoted about split pivot 64 in a generally distal direction. Such distal movement of bifurcated portion 66 of trigger 62 urges transverse pin 68 distally, thereby urging knife collar 166 distally. Distal urging of knife collar 166 urges proximal foot 163 of knife bar 162 to translate through elongated cut-out 150 (FIG. 8) of drive bar 142, thereby translating knife bar 162 and knife 164 distally through shaft 80 and relative to end effector assembly 100 from the retracted position to the extended position to cut tissue grasped between jaw members 110, 120.

A biasing member 169 is disposed about drive bar 142 between knife collar 166 and rotation wheel 72 of rotating assembly 70 such that, upon release of trigger 62, trigger 62 is returned under bias to the un-actuated position wherein bifurcated portion 66 is pivoted about split pivot 64 in a generally proximal direction to pull knife collar 166, knife bar 162, and knife 164 proximally, thereby returning knife 164 to the retracted position.

Shaft 80 defines a proximal portion 82 that extends into housing 20 and is engaged with rotation wheel 72 of rotating assembly 72 to longitudinally fix shaft 80 relative to housing 20. A pair of opposed longitudinal slots 84 are defined through proximal portion 82 of shaft 80, the importance of which are detailed below. As mentioned above, the distal end of shaft 80 engages jaw members 110, 120 of end effector assembly 100. Further, an insulative plate 86 may be engaged to the distal end of shaft 80. Insulative plate 86 extends along jaw flange 124 of jaw member 120, facilitates the support of jaw members 110, 120 at the distal end of shaft 80, and facilitates the electrical insulation of energizable member 220 of monopolar assembly 200 from end effector assembly 100 in the storage condition of monopolar assembly 200.

With reference to FIGS. 1, 2, and 6-8, monopolar assembly 200 includes a sheath assembly 210 and an energizable member 220. Sheath assembly 210 includes a proximal ferrule 212 and an elongated insulative sheath 214. Proximal ferrule 212 includes a body 215 having an annular flange 216 extending radially outwardly from body 215 at the proximal end of body 215. Annular flange 216 is retained within an annular slot 22 defined within housing 20 to fix proximal ferrule 212 in position relative to housing 20. Elongated insulative sheath 214 is slidably disposed about shaft 80 and extends into proximal ferrule 212. Elongated insulative sheath 214 defines a body portion 217 and an enlarged-diametered distal portion 218 extending distally from body portion 217. An annular step 219 is defined at the interface between body portion 217 and enlarged-diametered distal portion 218 of elongated insulative sheath 214. A proximal hub 230 is secured to the proximal end of elongated insulative sheath 214. As detailed below, proximal hub 230 is slidable within ferrule 212 to thereby slide elongated insulative sheath 214 relative to proximal ferrule 212. More specifically, elongated insulative sheath 214 is selectively movable about and relative to proximal ferrule 212, shaft 80 and end effector assembly 100 between a storage position (FIG. 2), wherein elongated insulative sheath 214 is disposed proximally of end effector assembly 100, and a use position (FIG. 33), wherein elongated insulative sheath 214 is substantially disposed about end effector assembly 100.

Energizable member 220 of monopolar assembly 200 includes a proximal cap 222, a proximal shaft 224, an energizable element 226, and an insulative sleeve 228. Proximal cap 222 is engaged to proximal shaft 224 at the proximal end thereof and is operably engaged with deployment and retraction mechanism 300 for selectively deploying and retracting monopolar assembly 200. Proximal shaft 224 extends from proximal cap 222 distally through housing 20. Energizable element 226 extends through proximal shaft 224 and distally therefrom to a distal tissue-treating portion 227. Energizable element 226 is coupled to the source of energy (not shown) and monopolar activation assembly 180 (FIG. 5) via one or more wires (not shown). As detailed below, distal tissue-treating portion 227 of energizable element 226 of energizable member 220 functions as the active electrode of monopolar assembly 200. Distal tissue-treating portion 227 of energizable member 220 may be hook-shaped (as shown), or may define any other suitable configuration, e.g., linear, ball, circular, angled, etc. Insulative sleeve 228 is disposed about at least a portion of energizable element 226, proximally of distal tissue-treating portion 227 so as to facilitate the electrical insulation of energizable element 226 from its surroundings.

Energizable member 220 is disposed on the inner-edge side of the curved jaw bodies 111, 121 of jaw members 110, 120 of end effector assembly 100 and is movable relative thereto between a storage position (FIG. 2), wherein distal tissue-treating portion 227 of energizable member 220 is positioned adjacent insulative plate 86 and proximal flanges 114, 124 of jaw members 110, 120 of end effector assembly 100, and a use position (FIG. 33), wherein distal tissue-treating portion 227 of energizable member 220 extends distally from end effector assembly 100 to facilitate treating tissue therewith. In the storage position (FIG. 2), insulative plate 86, jaw bodies 111, 121 of jaw members 110, 120, and insulative sleeve 228 serve to electrically-insulate distal tissue-treating portion 227 of energizable member 220 from electrically-conductive surfaces 112, 122 of jaw members 110, 120, respectively. In the use position (FIG. 33), elongated insulative sheath 214 of sheath assembly 210 serves to electrically insulate end effector assembly 100 from distal tissue-treating portion 227 of energizable member 220, while distal tissue-treating portion 227 extends distally from end effector assembly 100. Further, in the use position (FIG. 33), energy may be supplied to distal tissue-treating portion 227 of energizable member 220, e.g., via activation of either of the activation switches 182 of monopolar activation assembly 180 (FIG. 5), for treating tissue in the monopolar mode of operation.

Figures 32, 33:
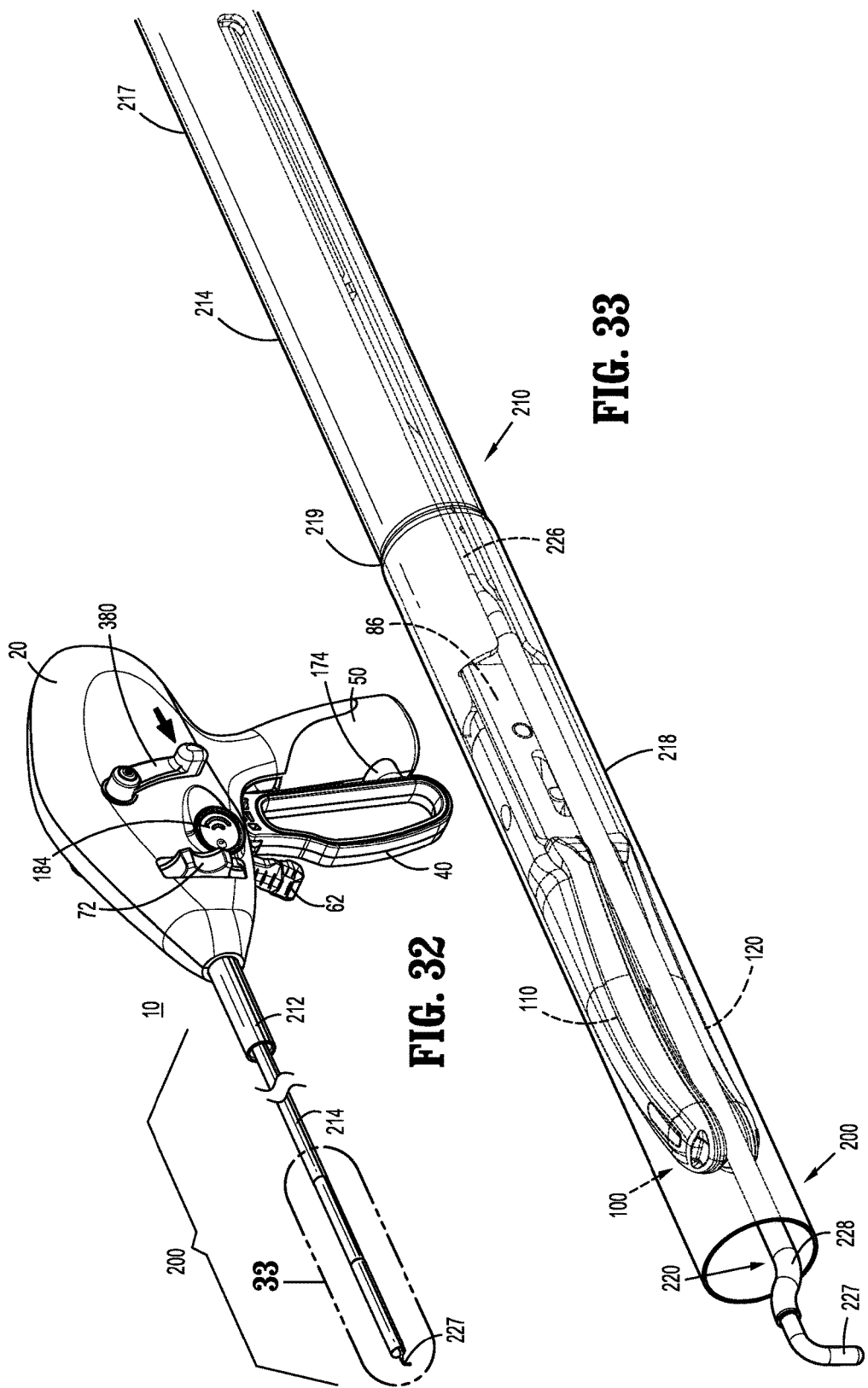
FIG. 32 is a front, perspective view of the surgical instrument of FIG. 1 with the monopolar assembly thereof disposed in the use condition.
FIG. 33 is an enlarged, perspective view of the area of detail indicated as "33" in FIG. 32.
Figure 34:
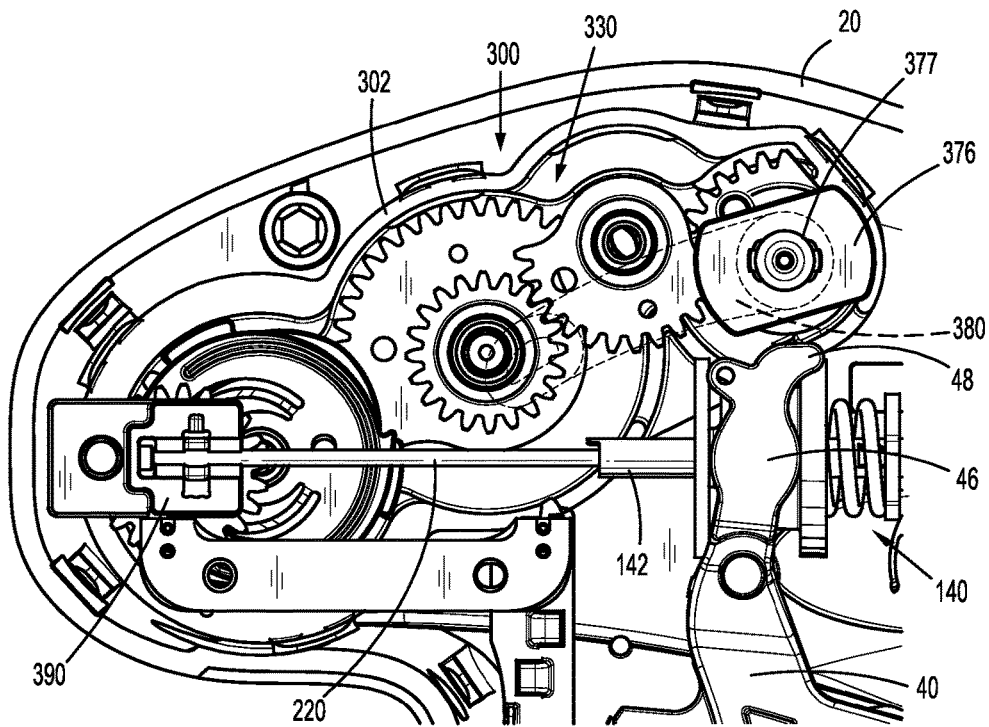
FIG. 34 is a side view of the proximal end of the surgical instrument of FIG. 1 with portions removed and the monopolar assembly disposed in the storage condition.
Figure 35:
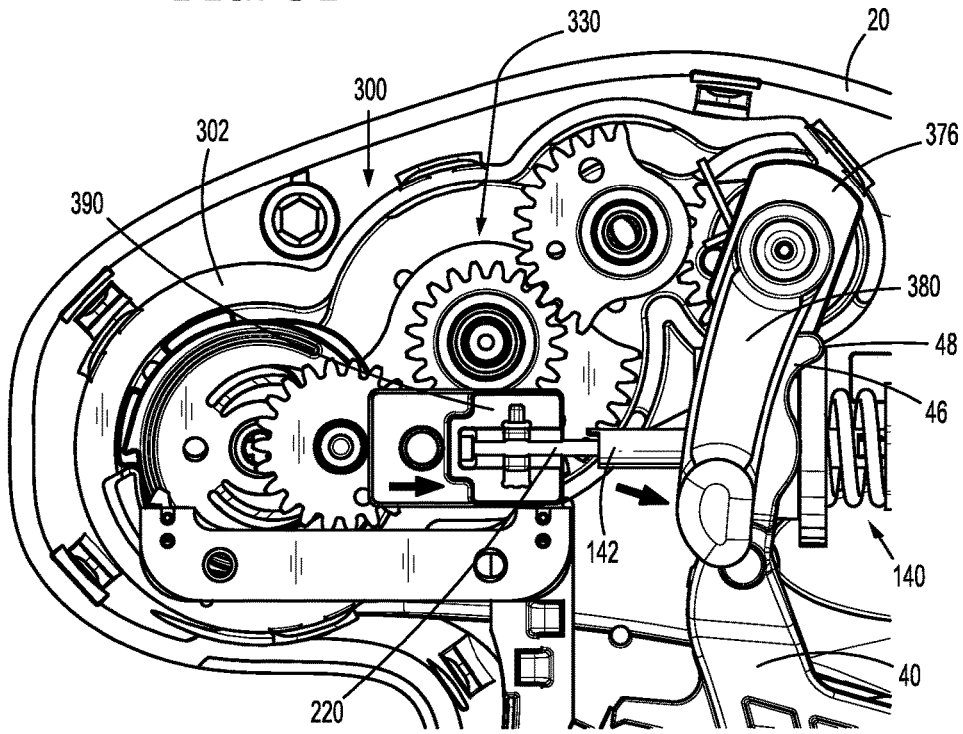
FIG. 35 is a side view of the proximal end of the surgical instrument of FIG. 1 with portions removed and the monopolar assembly disposed in the use condition.

An engagement pin 232 extends transversely from either side of proximal shaft 224 of energizable member 220. Engagement pin 232 extends through opposed longitudinal slots 152 of drive bar 142 and opposed longitudinal slots 84 of shaft 80 and is engaged within proximal hub 230 of sheath assembly 210 at each end of engagement pin 232, thereby securing sheath assembly 210 and energizable member 220 to one another. Thus, with proximal hub 230 and engagement pin 232 securing sheath assembly 210 and energizable member 220 with one another, and with proximal cap 222 of energizable member 220 operably coupled to deployment and retraction mechanism 300, deployment and retraction mechanism 300 is operable to cooperatively translate sheath assembly 210 and energizable member 220 between their respective storage positions, collectively the storage condition of monopolar assembly 200 (FIG. 2), and their respective use conditions, collectively the use condition of monopolar assembly 200 (FIG. 33). Various safety features may be employed for this purpose and are described hereinbelow.

With reference to FIG. 5, monopolar activation assembly 180, as noted above, includes a pair of monopolar activation switches 182. Monopolar activation switches 182 are positioned adjacent windows 24 defined within housing 20 on either side thereof. A depressible button 184 is operably coupled within each window 24 and extends outwardly therefrom. Depressible buttons 184 are selectively depressible from the exterior of housing 20 and, upon sufficient depression, are urged into contact with the respective monopolar activation switch 182 to activate that monopolar activation switch 182. Monopolar activation switches 182 are coupled to one another via a flex circuit 185 that extends along the inner perimeter of housing 20 about deployment and retraction mechanism 300. Monopolar activation assembly 180 further includes a connector member 186 and is coupled to a safety assembly 188 having proximal and distal safety switches 189a, 189b. Connector member 186 is coupled to the source of energy (not shown) and energizable element 226 of monopolar assembly 200 (FIG. 6) via one or more wires (not shown) to enable the selective supply of energy to energizable element 226 upon activation of either of monopolar activation switches 182. Safety switches 189a, 189b, as detailed below, are coupled to bipolar activation assembly 170 and monopolar activation assembly 180, respectively, via one or more wires (not shown) such that bipolar energy may only be supplied to jaw members 110, 120 (FIG. 6) when monopolar assembly 200 is disposed in the storage condition (FIG. 2), and such that monopolar energy may only be supplied to energizable member 220 (FIG. 6) when monopolar assembly 200 is disposed in the use condition (FIG. 33).

Referring to FIGS. 1, 3, 6, and 8, rotating assembly 70 includes rotation wheel 72 that is rotatably disposed but longitudinally constrained within a vertically-oriented slot 26 defined within housing 20. Rotation wheel 72 extends at least partially through slot 26 on either side of housing 20 to enable manipulation of rotation wheel 72 on either exterior side of housing 20. Rotation wheel 72, as noted above, is mounted about the proximal end of shaft 80. Thus, with rotation wheel 72 fixed about shaft 80, with end effector assembly 100 engaged at the distal end of shaft 80, with engagement pin 232 engaged to sheath assembly 210 and energizable member 220 of monopolar assembly 200 and extending through opposed longitudinal slots 152 of drive bar 142, and with proximal foot 163 of knife bar 162 extending through elongated cut-out 150 (FIG. 8) of drive bar 142, shaft 80, end effector assembly 100, drive assembly 140, knife assembly 160, and monopolar assembly 200 are rotatably fixed relative to one another and are capable of being rotated relative to housing 20 and in cooperation with one another via rotation of rotation wheel 72.

As shown in FIG. 6, a tube guide 90 fixedly disposed within shaft 80 may also be provided to facilitate the alignment of the various internal sliding components disposed within shaft 80, e.g., drive bar 142, knife assembly 160, and energizable member 220. More specifically, tube guide 90 defines a central lumen (not shown) configured to slidably receive drive bar 142 and first and second channels (not shown) defined within the outer periphery thereof and extending longitudinally therealong to slidably receive knife assembly 160 and energizable member 220, respectively. U.S. patent application Ser. No. 14/196,066, previously incorporated herein by reference, details a tube guide suitable for this purpose.

Referring generally to FIGS. 1, 3-5, and 7-29, deployment and retraction mechanism 300 is configured for selectively transitioning monopolar assembly 200 between its storage condition and its use condition, although deployment and retraction mechanism 300 may similarly be used in connection with any suitable surgical instrument for deploying and retracting any suitable deployable component(s). Deployment and retraction mechanism 300 generally includes a gear box 302 mounted within housing 20, a gear assembly 330 operably disposed within gear box 302, a pair of rotatable actuators 380 operably coupled to the input of gear assembly 330, and a slider 390 configured to operably engage monopolar assembly 200 with the output of gear assembly 330. As will become apparent in view of the following, deployment and retraction mechanism 300 is configured to enable both deployment and retraction of monopolar assembly 200 in a push-push manner, e.g., wherein monopolar assembly 200 is both deployed and retracted by pushing either of rotatable actuators 380 in the same direction, return monopolar assembly 200 back to its previous condition in the event of an incomplete actuation, retain monopolar assembly 200 in the use condition or the storage condition upon a full actuation, provide an advantageous gear ratio for deploying and retracting monopolar assembly 200, actuate movable handle 40 to approximate jaw members 110, 120 prior to deployment of monopolar assembly 200 if necessary, permit the supply of energy to energizable member 220 only when monopolar assembly 200 is disposed in the use condition, and permit the supply of energy to jaw members 110, 120 only when monopolar assembly 200 is disposed in the storage condition.

Figure 9:
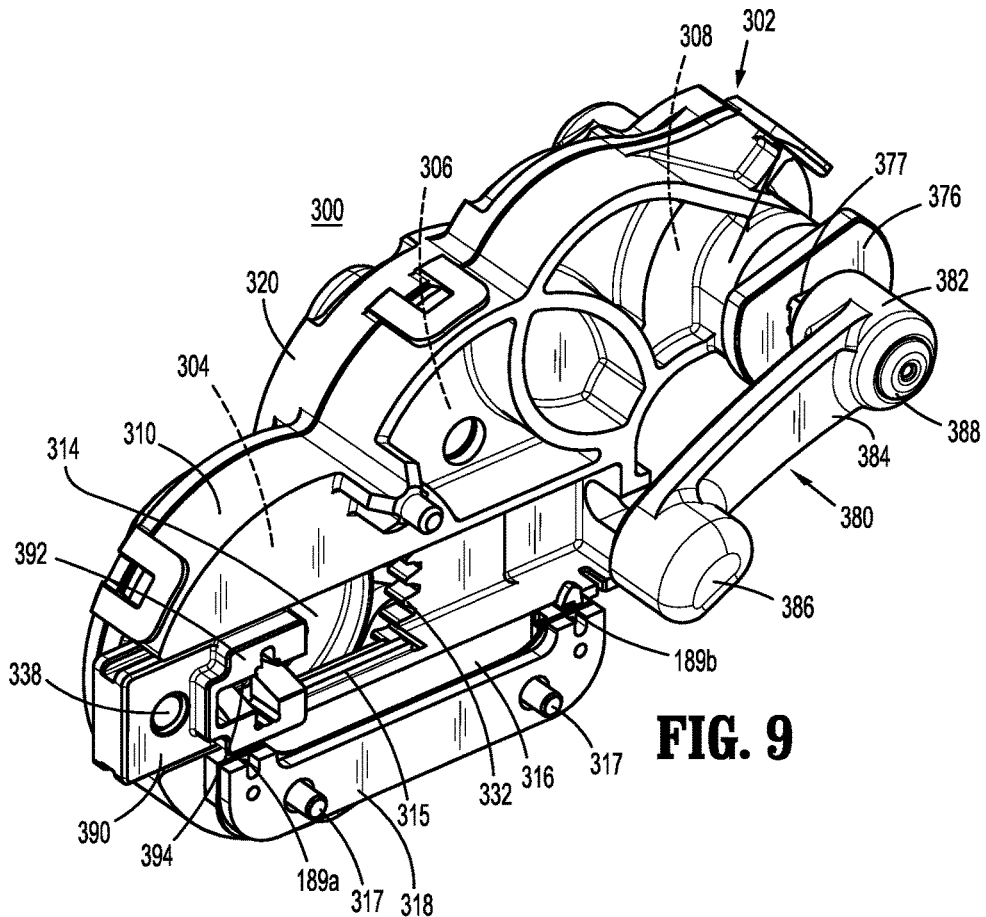
FIG. 9 is a rear, perspective view from a first side of the deployment and retraction mechanism of FIG. 7.
Figure 10:
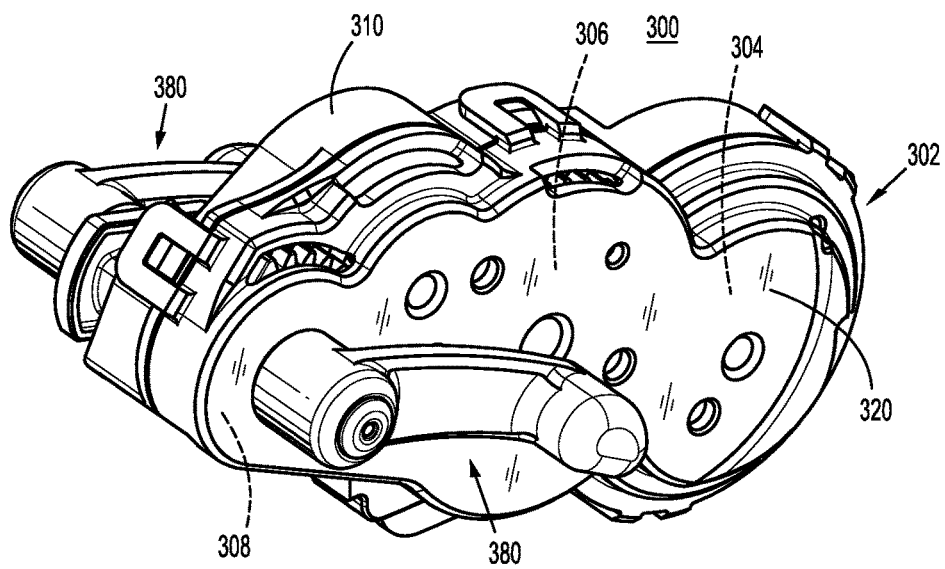
FIG. 10 is a front, perspective view from a second side of the deployment and retraction mechanism of FIG. 7.
Figure 11:
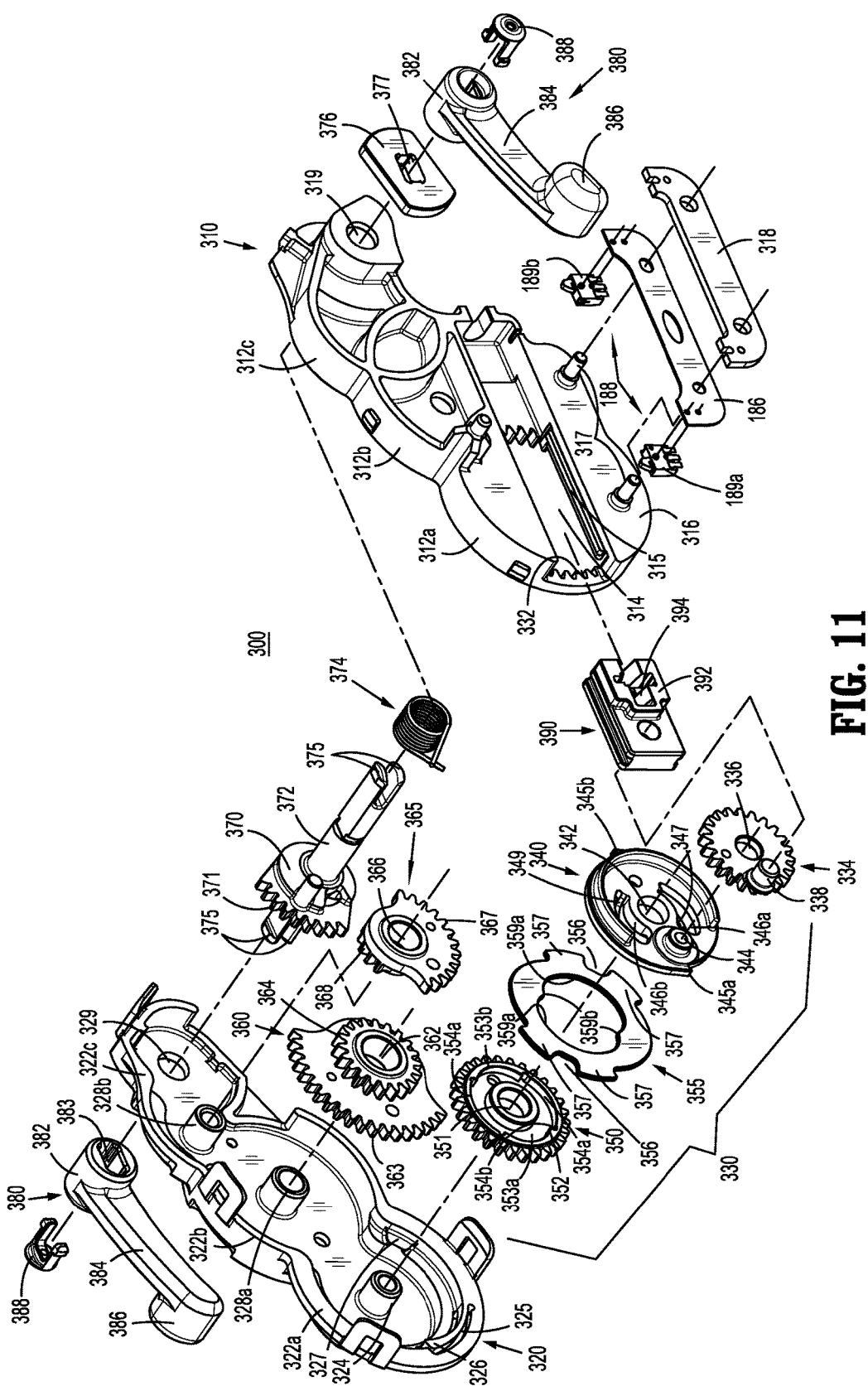
FIG. 11 is an exploded, perspective view of the deployment and retraction mechanism of FIG. 7.
Figure 12:
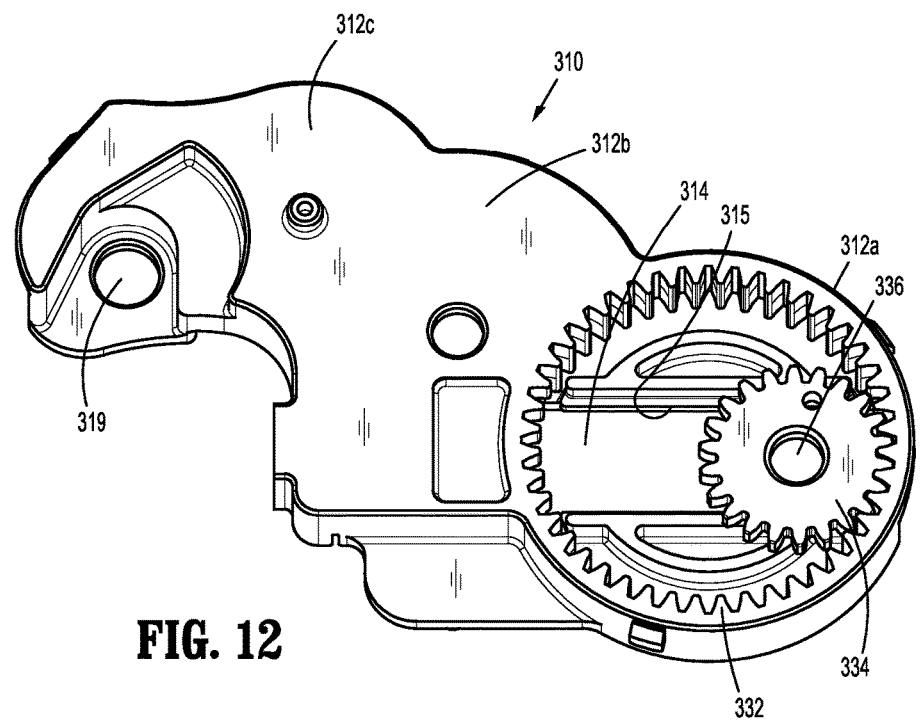
FIG. 12 is a perspective view of the first housing component of the deployment and retraction mechanism of FIG. 7 having a planet gear operably engaged with the ring gear thereof.
Figure 13:
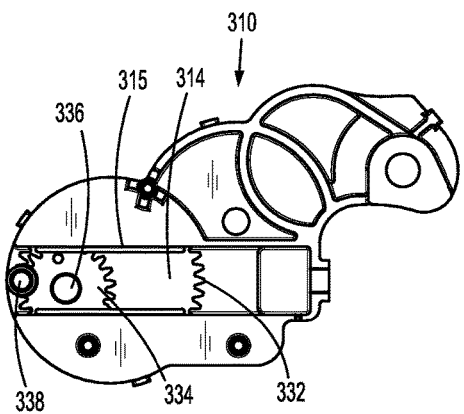
FIGS. 13-16 are side views of the first housing component and planet gear of FIG. 12 illustrating movement of the planet gear from a proximal position corresponding to the storage condition of the monopolar assembly to a distal position corresponding to a use condition of the monopolar assembly.
Figure 14:
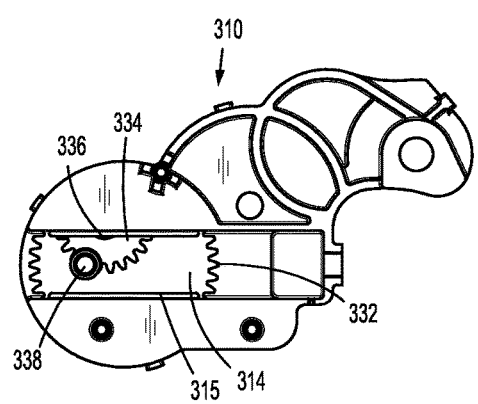
Figure 15:
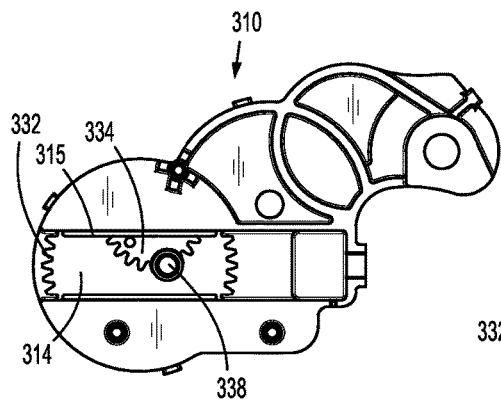
Figure 16:
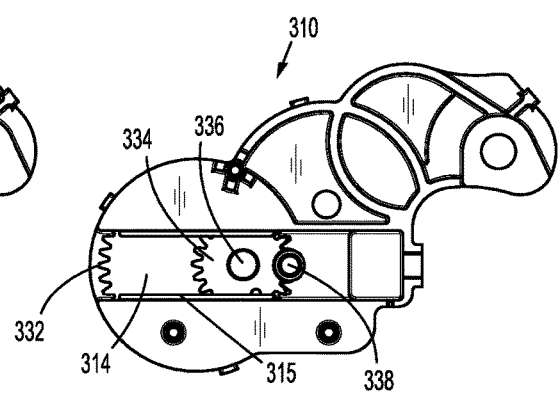
Figure 17:
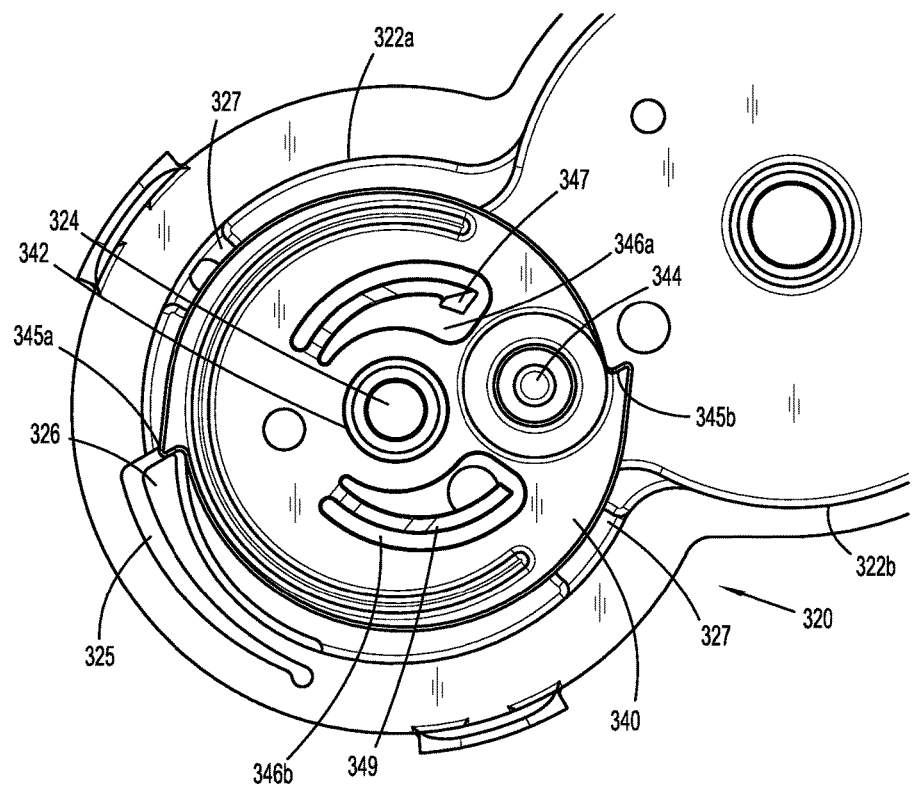
FIG. 17 is an enlarged, side view of a portion of the second housing component of the deployment and retraction mechanism of FIG. 7 having a carrier member operably engaged therewith.
Figure 24:
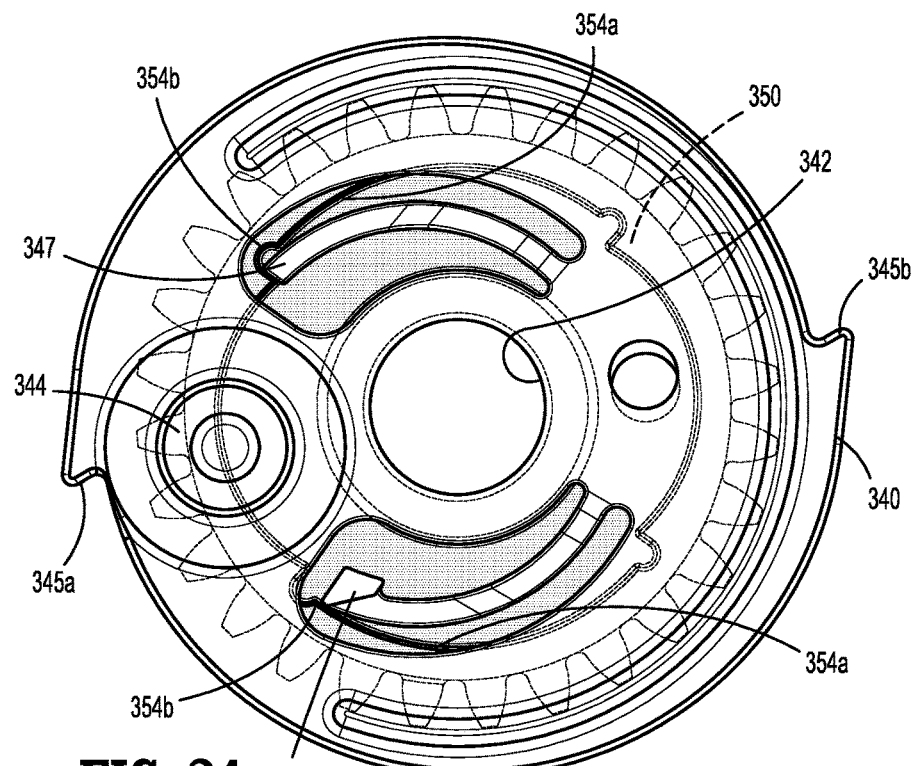
FIGS. 24 and 25 are side views of the ratchet gear and carrier member of the deployment and retraction mechanism of FIG. 7 operably engaged with one another for rotation in forward and reverse directions, respectively.
Figure 25:
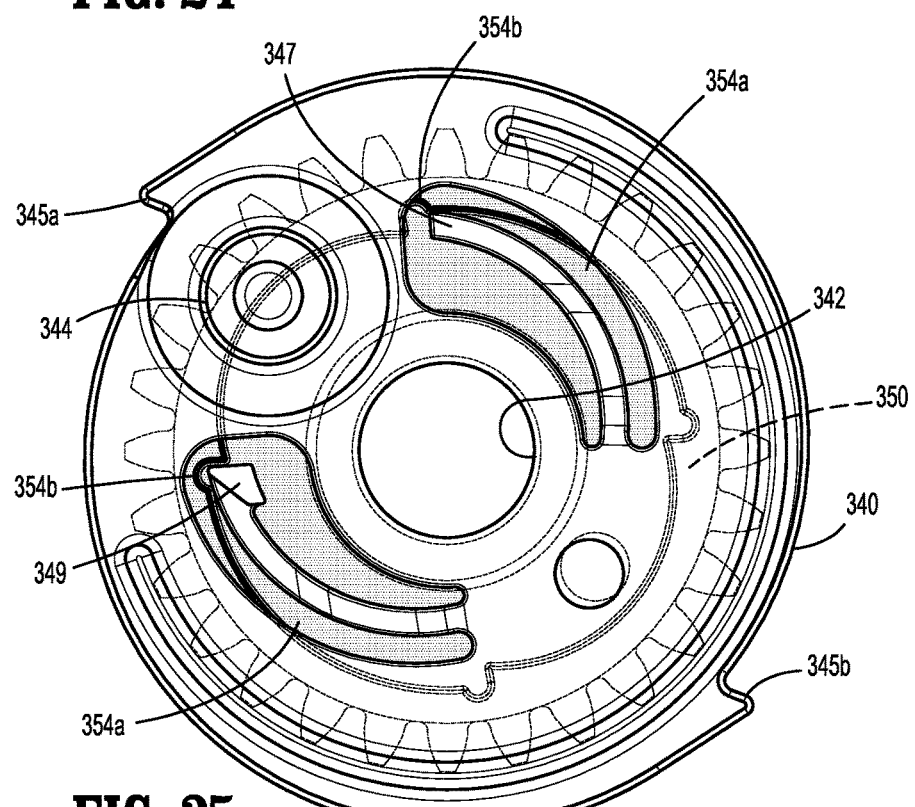

Referring to FIGS. 9-11, gear box 302 of deployment and retraction mechanism 300 is formed from first and second housing components 310, 320, respectively, secured to one another in snap-fit engagement, although other configurations are also contemplated, to enclose and retain gear assembly 330 therein. First and second housing components 310, 320 each define three overlapping disc-shaped cavity portions 312a, 312b, 312c, and 322a, 322b, 322c that cooperate to define three overlapping cavities 304, 306, 308 within gear box housing 302. First housing component 310 further includes a longitudinal slot 314, a support portion 316, and a distal aperture 319.

First disc-shaped cavity portion 312a of first housing component 310 includes ring gear 332 of gear assembly 330 disposed on the inwardly-facing surface thereof. As detailed below, planet gear 334, carrier member 340, ratchet gear 350, and disengagement plate 355 of gear assembly 330 are retained within first cavity 304 of gear box 302 in operable engagement with ring gear 332. Longitudinal slot 314 is defined through first housing component 310 adjacent first disc-shaped cavity portion 312a to provide access to the interior area defined within ring gear 332. A longitudinal track 315 defined within first housing component 310 on either side of longitudinal slot 314 and extending therealong is configured to operably engage slider 390 to guide longitudinal translation of slider 390 between the proximal and distal ends of longitudinal slot 314.

Second disc-shaped cavity portion 312b of first housing component 310 is disposed adjacent to and in communication with first disc-shaped cavity portion 312a. Second cavity 306 of gear box 302 is configured to retain first and second compound gears 360, 365, respectively, of gear assembly 330 in operable engagement with those components of gear assembly 330 retained within cavity 304, e.g., ring gear 332, planet gear 334, carrier member 340, ratchet gear 350, and disengagement plate 355.

Third disc-shaped cavity portion 312c of first housing component 310 is disposed adjacent to and in communication with second disc-shaped cavity portion 312b. Third cavity 308 of gear box 302 is configured to retain drive gear 370 of gear assembly 330 in operable engagement with first and second compound gears 360, 365, respectively, of gear assembly 330. Third disc-shaped cavity portion 312c of first housing component 310 further defines distal aperture 319 therethrough that is configured to receive pin 372, which extends through gear box 302 in order to operably couple rotatable actuators 380 to one another and gear assembly 330, as detailed below.

Support portion 316 of first housing component 310 includes a pair of posts 317 extending outwardly therefrom that are configured to support safety assembly 188. A back plate 318 is also provided to retain safety assembly 188 on posts 317 and in position adjacent first housing component 310 such that proximal and distal safety switches 189a, 189b of safety assembly 188 are maintained in position adjacent the respective proximal and distal ends of longitudinal slot 314. Support portion 316 of first housing component 310 may additionally include cut-outs, slots, apertures, channels, or other suitable features for routing wires (not shown) to/from proximal and distal safety switches 189a, 189b and/or energizable element 226 of monopolar assembly 200 (FIG. 6).

Second housing component 320, as mentioned above, defines three overlapping disc-shaped cavity portions 322a, 322b, 322c that are configured to cooperate with respective disc-shaped cavity portions 312a, 312b, 312c of first housing component 310 upon engagement of first and second housing components 310, 320 to define overlapping cavities 304, 306, 308 within gear box 302. First disc-shaped cavity portion 322a of second housing component 320 defines a first post 324 extending inwardly therefrom that is configured to rotatably support carrier member 340 and ratchet gear 350 of gear assembly 330 with disengagement plate 355 of gear assembly 330 disposed therebetween. Second housing component 320 further includes a cut-out 325 adjacent first disc-shaped cavity portion 322a and a first pawl 326 extending into cut-out 325. First pawl 326 is formed integrally with second housing component 320 to define a living hinge therebetween, thus permitting the free end of first pawl 326 to flex within cut-out 325 and relative to second housing component 320. The living hinge defined between first pawl 326 second housing component 320 is configured such that first pawl 326 is biased inwardly towards first post 324.

Second housing component 320 further includes a pair of radially-opposed protrusions 327 disposed on the interior surface thereof that are positioned about the perimeter of first disc-shaped cavity portion 322a. Disengagement plate 355 of gear assembly 330 includes a corresponding pair of radially-opposed gaps 356 defined between each pair of tabs 357 thereof that are configured to receive protrusions 327 to seat disengagement plate 355 within second housing component 320 in fixed rotational orientation relative to second housing component 320, the important of which is detailed below.

Second disc-shaped cavity portion 322b of second housing component 320 defines a second post 328a extending inwardly therefrom, while a third post 328b extends inwardly from the overlapping region defined between second and third disc-shaped cavity portions 322b, 322c. Second post 328a is configured to rotatably support first compound gear 360 of gear assembly 330 in operable engagement with the components of gear assembly 330 retained within cavity 304, e.g., ring gear 332, planet gear 334, carrier member 340, ratchet gear 350, and disengagement plate 355, while third post 328b is configured to rotatably support second compound gear 365 in operable engagement with first compound gear 360.

Third disc-shaped cavity portion 322c of second housing component 320 further defines a distal aperture 329 therethrough that is configured to receive pin 372, which extends through gear box 302 in order to operably couple rotatable actuators 380 to one another and gear assembly 330, as detailed below. Distal apertures 319, 329 of third disc-shaped cavity portions 312c, 322c of first and second housing components 310, 320, respectively, are aligned with one another and positioned such that drive gear 370 of gear assembly 330 is retained within third cavity 308 in operable engagement with second compound gear 365 of gear assembly 330.

Gear assembly 330 includes ring gear 332, planet gear 334, carrier member 340, ratchet gear 350, disengagement plate 355, first and second compound gears 360, 365, and drive gear 370. With reference to FIGS. 11-16, ring gear 332, as mentioned above, is disposed on the inwardly-facing surface of first disc-shaped cavity portion 312a of first housing component 310. Planet gear 334 is disposed in meshed engagement with ring gear 332 so as to permit orbiting of planet gear 334 about the interior perimeter of ring gear 332. Planet gear 334 defines a central aperture 336 about which planet gear 334 is rotatably mounted on off-center pivot 344 of carrier member 340. Planet gear 334 further includes an off-center pin 338 extending therefrom and through longitudinal slot 314 of first housing component 310 to rotatably support slider 390 thereon. Off-center pin 338 serves as the output of gear assembly 330.

The ratio of the pitch diameters of ring gear 332 and planet gear 334 is 2:1 such that as planet gear 334 is orbited about the interior perimeter of ring gear 332, off-center pin 338 of planet gear 334 is translated linearly through longitudinal slot 314 of first housing component 310. More specifically, upon a first half-orbit of planet gear 334 within ring gear 332, off-center pin 338 is translated from the proximal end of longitudinal slot 314 to the distal end of longitudinal slot 314. Upon completion of the second half-orbit of planet gear 334 within ring gear 332 to return planet gear 334 back to its initial position, off-center pin 338 is translated from the distal end of longitudinal slot 314 back to the proximal end of longitudinal slot 314. As noted above, off-center pin 338 of planet gear 334 supports slider 390 thereon such that each half-orbit of planet gear translates slider 390 through track 315 from one end of longitudinal slot 314 to the other end of longitudinal slot 314.

Referring to FIGS. 7, 11, 19, and 20, carrier member 340 of gear assembly 330 defines a central aperture 342 about which carrier member 340 is rotatably supported on first post 324 of second housing component 320 adjacent planet gear 334. As noted above, off-center pivot 344 of carrier member 340 rotatably supports planet gear 334 thereon. Carrier member 340 is generally disc-shaped except that the outer annular periphery of carrier member 340 is irregular so as to define a pair of tangentially-facing, radially-opposed shoulders 345a, 345b thereon. Carrier member 340 further includes a pair of opposed cut-outs 346a, 346b defined radially between central aperture 342 and the outer annular periphery of carrier member 340, and second and third pawls 347, 349 defined within respective cut-outs 346a, 346b.

Second and third pawls 347, 349 are integrally formed with carrier member 340 via respective living hinges so as to permit the free ends of second and third pawls 347, 349 to flex within respective cut-outs 346a, 346b and relative to carrier member 340.

Figure 7:
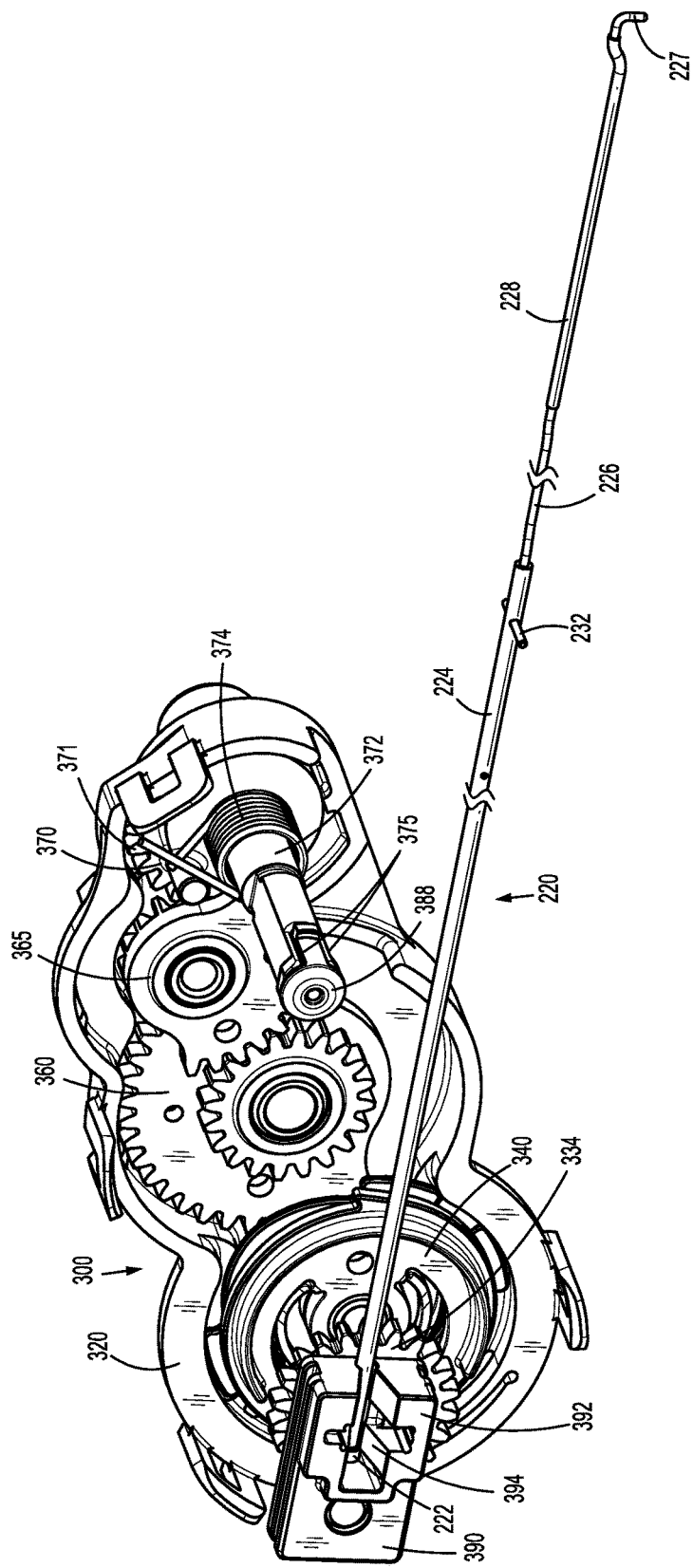
FIG. 7 is a perspective view of the deployment and retraction mechanism and the monopolar assembly of the surgical instrument of FIG. 1 with portions removed.

With reference to FIGS. 7, 11, and 18, ratchet gear 350 defines a central aperture 351 about which ratchet gear 350 is rotatably supported on first post 324 of second housing component 320 adjacent the interior surface of second housing component 320. A face 352 of ratchet gear 350 has a recessed portion 353a defining a perimeter wall 353b. Perimeter wall 353b defines a pair of radially-opposed, arcuate cut-outs 354a, each having a notch 354b disposed at either end thereof.

Figure 26:
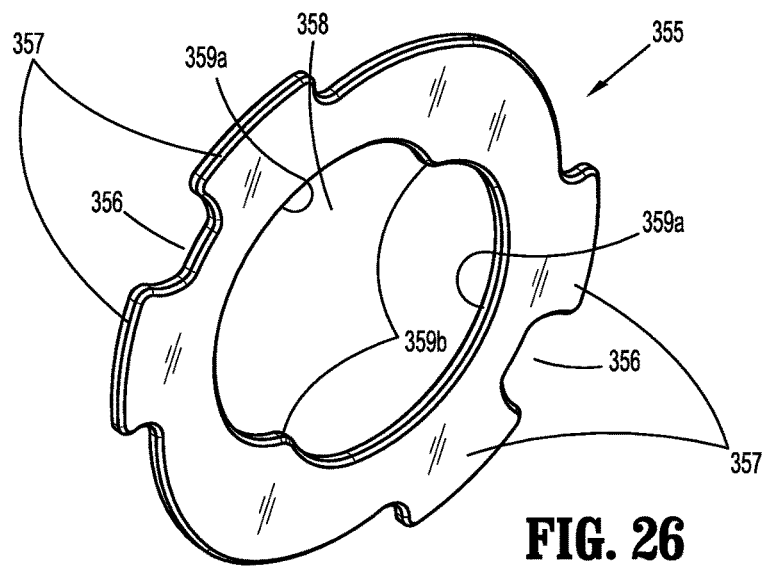
FIG. 26 is a side, perspective view of the disengagement plate of the deployment and retraction mechanism of FIG. 7.
Figure 27:
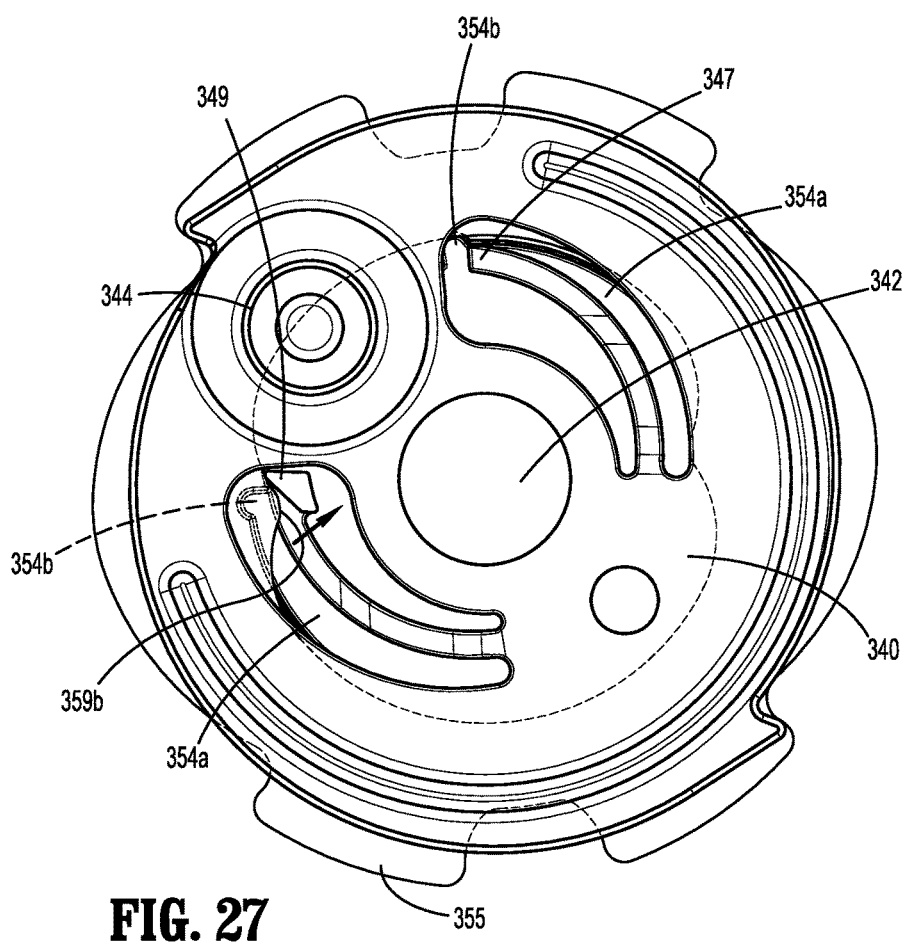
FIG. 27 is a side view of the carrier member and disengagement plate of the deployment and retraction mechanism of FIG. 7 operably positioned relative to one another to disengage the carrier member.

Referring to FIGS. 7, 11 and 26, disengagement plate 355 defines a central opening 358 defined by a pair of opposed arcuate segments 359a interconnected with one another at opposed pinch points 359b. Disengagement plate 355 further includes first and second pairs of opposed, radially-outwardly extending tabs 357. Each pair of tabs 357 defines a gap 356 therebetween that, as mentioned above, is configured to receive one of the protrusions 327 of second housing component 320 to seat disengagement plate 355 within second housing component 320 in fixed rotational orientation relative to gear box 302.

With reference to FIGS. 7, 11 and 21, first compound gear 360 defines a central aperture 362 about which first compound gear 360 is rotatably supported on second post 328a of second housing component 320. First compound gear 360 further includes a semi-annular outer gear portion 363 disposed in meshed engagement with ratchet gear 350, and an annular inner gear portion 364. Second compound gear 365 defines a central aperture 366 about which second compound gear 365 is rotatably supported on third post 328b of second housing component 320. Second compound gear 365 further includes a semi-annular outer gear portion 367 that is disposed in meshed engagement with annular inner gear portion 364 of first compound gear 360, and an annular inner gear portion 368.

Drive gear 370 is mounted on pin 372, which extends through and is rotatable relative to apertures 319, 329 of first and second housing components 310, 320, respectively. Pin 372 serves as the input of gear assembly 330. Drive gear 370 includes a semi-annular gear portion 371 that is disposed in meshed engagement with annular inner gear portion 368 of second compound gear 365. A torsion spring 374 is operably disposed about pin 372 and is positioned within gear box 302 between drive gear 370 and first housing component 310. The ends of pin 372 each define a bifurcated configuration having a pair of spaced-apart arms 375. A closure plate 376 defining a rectangular aperture 377 is disposed about one of the ends of pin 372 and is rotationally keyed thereto via receipt of arms 375 within rectangular aperture 377 of closure plate 376. Closure plate 376 is disposed about pin 372 within housing 20 between first housing component 310 of gear box 302 and the interior surface of housing 20. As an alternative to closure plate 376, other suitable closure mechanisms are also contemplated such as, for example, a cam/slider mechanism.

A portion of each of the ends of pin 372 extends from first and second housing components 310, 320 through apertures 28 defined within housing 20 on either side thereof. Bases 382 of actuators 380 are mounted on the ends of pin 372 exteriorly of housing 20 and are rotationally keyed thereto via receipt of arms 375 within rectangular apertures 383 defined within bases 382 of actuators 380. Lever portions 384 of actuators 380 extend from bases 382 and define enlarged free ends 386 to facilitate manipulation thereof. Spring clips 388 extend through rectangular apertures 383 of actuators 380 and engage the interior surface of housing 20 on either side thereof to rotatably couple actuator 380 to housing 20 and retain actuators 380 about pin 372.

With reference to FIGS. 7, 11, and 28-30, slider 390, as noted above, is positioned adjacent longitudinal slot 314 of first housing component 310 and is operably engaged within track 315 of first housing component 310 to enable slider 390 to translate relative to first housing component 310 between the proximal and distal ends of longitudinal slot 314. Slider 390 includes a hub 392 defining a recess 394 that is configured to receive proximal cap 222 of energizable member 220 of monopolar assembly 200 in rotatable engagement therewith. Thus, monopolar assembly 200, along with shaft 80, end effector assembly 100, drive assembly 140, and knife assembly 160, may be rotated together relative to housing 20 and deployment and retraction mechanism 300, e.g., via rotation of rotation wheel 72.

Referring to FIGS. 11 and 21-30, as can be appreciated in view of the above, gear box 302 is configured so as to operably retain semi-annular gear portion 371 of drive gear 370 in meshed engagement with annular inner gear portion 368 of second compound gear 365, semi-annular outer gear portion 367 of second compound gear 365 in meshed engagement with annular inner gear portion 364 of first compound gear 360, and semi-annular outer gear portion 363 of first compound gear 360 in meshed engagement with ratchet gear 350. Further, ratchet gear 350, disengagement plate 355, and carrier member 340 are stacked in operable engagement with one another within cavity 304 of gear box 302 with the free ends of second and third pawls 347, 349 of carrier member 340 each initially disposed within one of the cut-outs 354a of ratchet gear 350. In addition, planet gear 334 is pivotably coupled to carrier member 340 at an off-center position relative thereto, is disposed in meshed engagement with ring gear 332, and is coupled to slider 390.

In operation, with monopolar assembly 200 disposed in the storage condition or the use condition, the free end of first pawl 326 is engaged with one of radially-opposed shoulders 345a, 345b of carrier member 340 to inhibit reverse rotation (e.g., counterclockwise rotation as viewed in FIG. 23) of carrier member 340, thereby fixing planet gear 334 and slider 390 in position and retaining monopolar assembly 200 in the storage condition or the use condition (see FIG. 23). More specifically, in the storage condition, first pawl 326 is engaged with radially-opposed shoulder 345a to retain monopolar assembly 200 in the storage condition, while, in the use condition, first pawl 326 is engaged with the other radially-opposed shoulder 345b to retain monopolar assembly 200 in the use condition.

Upon actuation of either or both actuators 380, e.g., upon distal urging of either or both of enlarged free ends 386 of actuators 380 relative to housing 20 to rotate actuators 380 in their forward directions, pin 372 is rotated relative to housing 20 in a forward direction to thereby rotate drive gear 370 in its forward direction which, in turn, drives rotation of second compound gear 365 in its forward direction. Such rotation of second compound gear 365 drives rotation of first compound gear 360 in its forward direction which, in turn, drives rotation of ratchet gear 350 in its forward direction. As ratchet gear 350 is rotated within cavity 302 in its forward direction, the free end of second pawl 347 of carrier member 340 is slid through the corresponding cut-out 354a of ratchet gear 350 until the free end of second pawl 347 is engaged within one of the notches 354b of ratchet gear 350 to couple carrier member 340 and ratchet gear 350 to one another (see FIG. 24). Thus, upon further forward rotation of ratchet gear 350, carrier member 340 is driven to rotate in its forward direction (e.g., clockwise as viewed in FIG. 23). With planet gear 334 pivotably coupled to carrier member 340 at an off-center position relative thereto, disposed in meshed engagement within ring gear 332, and supporting slider 390 thereon, rotation of carrier member 340 in its forward direction drives planet gear 334 to orbit in its forward direction within ring gear 332 to thereby translate slider 390 through longitudinal slot 314 to initiate deployment or retraction of monopolar assembly 200 (see FIGS. 28 and 29).

Upon a full actuation of actuator(s) 380, drive gear 370, second compound gear 365, first compound gear 360, and ratchet gear 350 are sufficiently rotated in their respective forward directions so as to rotate carrier member 340 through a one-half revolution in its forward direction. Such a one-half revolution of carrier member 340 in its forward direction drives planet gear 334 to orbit within ring gear 332 through a half-orbit, thereby translating slider 390 through longitudinal slot 314 from either the proximal or distal end thereof to the other of the proximal or distal end thereof to transition monopolar assembly 200 from the storage condition to the use condition or from the use condition to the storage condition, respectively. Upon completion of the one-half revolution of carrier member 340, first pawl 326 of second housing component 320 cams over the adjacent radially-opposed shoulder 345a, 345b of carrier member 340 ultimately falling into engagement therewith such that reverse rotation of carrier member 340 is inhibited, thereby retaining monopolar assembly 200 in the storage condition or the use condition (see FIG. 23). Further, in each of the two end rotational orientations of carrier member 340, e.g., the positions reached upon a one-half revolution of carrier member 340, carrier member 340 is oriented relative to disengagement plate 355 such that one of the pinch points 359b of disengagement plate 355 urges the free end of third pawl 349 inwardly towards the center of carrier member 340 (see FIG. 27). In this position, the free end of third pawl 349 is withdrawn from the corresponding cut-out 354a of ratchet gear 350 to thereby disengage carrier member 340 from ratchet gear 350.

Release of actuator(s) 380 after a full actuation allows the bias of torsion spring 374 to urge actuators 380 to rotate in a reverse direction back to their initial, proximal positions and likewise urges pin 372 to rotate relative to housing 20 in its reverse direction, thereby rotating drive gear 370, second compound gear 365, first compound gear 360, and ratchet gear 350 in their respective reverse directions. As noted above, however, carrier member 340 is inhibited from reverse rotation once the half-revolution thereof has been achieved, due to the engagement of first pawl 326 with one of the radially-opposed shoulders 345a, 345b of carrier member 340 (see FIG. 23). Thus, during reverse rotation of the above-noted components, carrier member 340 is maintained fixed relative to gear box 302. Such relative rotation of the above-noted components relative to carrier member 340 is permitted due to the fact that, as detailed above, upon completion of a full actuation, disengagement plate 355 serves to disengage carrier member 340 from ratchet gear 350. Accordingly, carrier member 340, planet gear 334, and slider 390 are retained in position to retain monopolar assembly 200 in its condition, while actuators 380, pin 372, drive gear 370, second compound gear 365, first compound gear 360, and ratchet gear 350 are returned to their initial positions.

Subsequent full actuations and releases of actuator(s) 380 may be effected to repeatedly transition monopolar assembly 200 between the storage condition and the use condition. As can be appreciated, upon each full actuation and release of actuators 380, actuators 380, pin 372, drive gear 370, second compound gear 365, first compound gear 360, and ratchet gear 350 are rotated in their respective forward directions from their initial positions to their end positions and then in their respective reverse directions from the end positions back to their initial positions. Carrier member 340 and planet gear 334, however, are rotatable in a single direction with each full actuation, and are rotated through a half-revolution and half-orbit, respectively, with each full actuation.

Should actuator(s) 380 be released after only a partial-actuation, e.g., prior to being rotated through a full actuation, torsion spring 374 urges pin 372 to rotated relative to housing 20 in a reverse direction thereof, thereby rotating drive gear 370, second compound gear 365, first compound gear 360, and ratchet gear 350 in their respective reverse directions, similarly as if a full actuation had been achieved. However, since carrier member 340 does not complete a one-half revolution in response to a partial actuation, first pawl 326 of second housing component 320 is not moved into engagement with one of the radially-opposed shoulders 345a, 345b of carrier member 340 to inhibit reverse rotation of carrier member 340, and carrier member 340 is not oriented such that one of the pinch points 359b of disengagement plate 355 urges the free end of third pawl 349 inwardly to disengage carrier member 340 from ratchet gear 350. Rather, upon reverse rotation of ratchet gear 350 after a partial-actuation, the free end of third pawl 349 of carrier member 340 is slid through the corresponding cut-out 354a of ratchet gear 350 until the free end of third pawl 349 is engaged within one of the notches 354b of ratchet gear 350 to couple carrier member 340 and ratchet gear 350 to one another (see FIG. 25). Thus, upon further rotation of ratchet gear 350 in its reverse direction under the bias of torsion spring 374, carrier member 340 is urged, similarly as ratchet gear 350, to rotate in its reverse direction to thereby drive planet gear 334 to orbit in its reverse direction and translate slider 390 back to its previous position, e.g., the position of slider 390 prior to the partial actuation. Put generally, the above-detailed feature returns monopolar assembly 200 back to its previous condition in the event of a partial actuation and, thus, avoids monopolar assembly 200 from stalling in an intermediate condition between the storage and use conditions.

Figure 28:
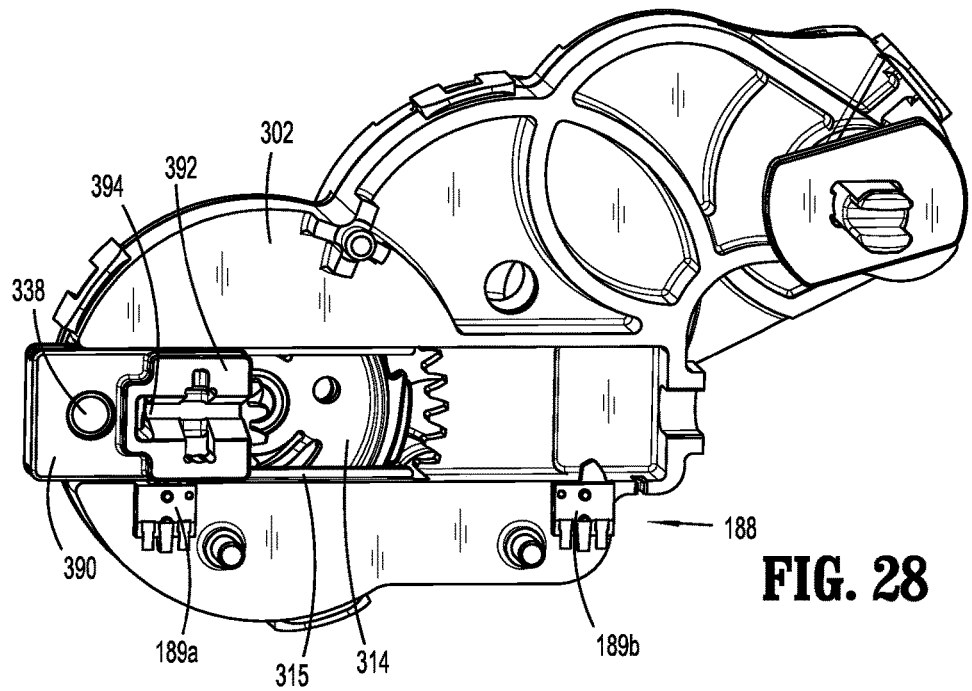
FIGS. 28 and 29 are side, perspective views of the deployment and retraction mechanism of FIG. 7 with the slider disposed in respective proximal and distal positions.
Figure 29:
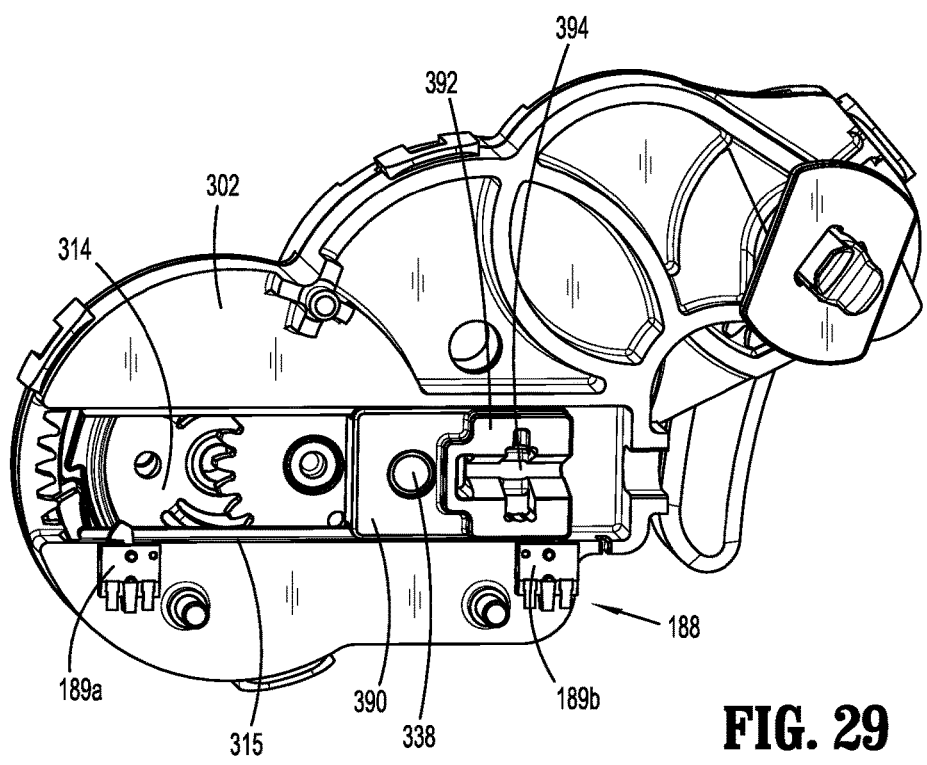
Figure 30:
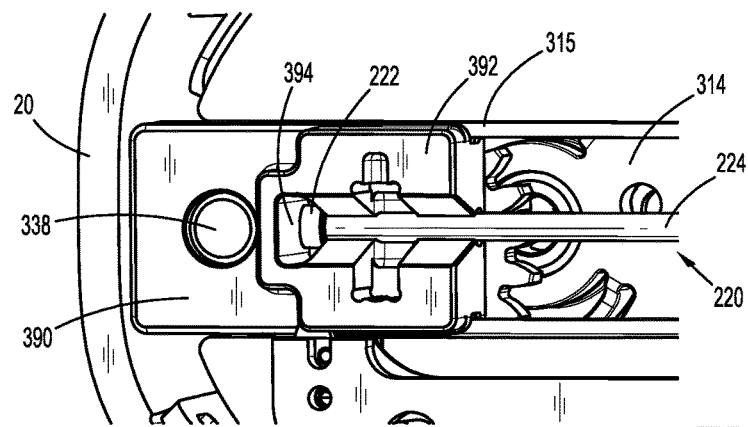
FIG. 30 is an enlarged, side, perspective view of a portion of the deployment and retraction mechanism of FIG. 7.
Figure 31:
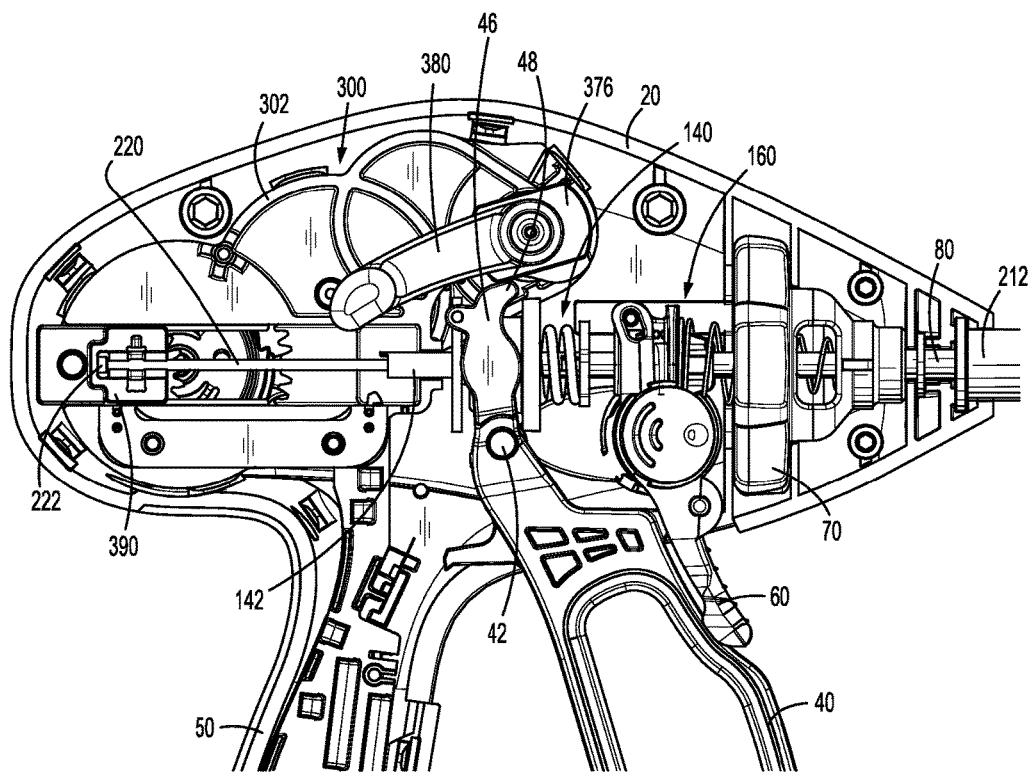
FIG. 31 is a side view of the proximal end of the surgical instrument of FIG. 1 with portions removed to illustrate the internal working components thereof.

With reference to FIGS. 28 and 29, as detailed above, safety assembly 188 is mounted on first housing component 310 of gear box 302 and includes proximal and distal safety switches 189a, 189b, respectively. Proximal safety switch 189a inhibits the supply of energy to surfaces 112, 122 of jaw members 110, 120 (FIG. 2), respectively, unless proximal safety switch 189a is activated, while distal safety switch 189b inhibits the supply of energy to energizable member 220 unless distal safety switch 189b is activated. Proximal safety switch 189a is operably positioned adjacent the proximal end of longitudinal slot 314 of first housing component 310 such that slider 390 activates proximal safety switch 189a only when disposed at the proximal end of longitudinal slot 314 (corresponding to the storage condition of monopolar assembly 200 (FIG. 32)). Distal safety switch 189b is operably positioned adjacent the distal end of longitudinal slot 314 of first housing component 310 such that slider 390 activates distal safety switch 189b only when disposed at the distal end of longitudinal slot 314 (corresponding to the use condition of monopolar assembly 200

(FIG. 32)). Thus, energy may only be supplied to surfaces 112, 122 of jaw members 110, 120 (FIG. 2), respectively, when monopolar assembly 200 (FIG. 32) is disposed in the storage condition, and energy may only be supplied to energizable member 220 of monopolar assembly 200 (FIG. 32) when monopolar assembly 200 (FIG. 32) is disposed in the use position.

With reference to FIGS. 1, 2, and 32-35, as also detailed above, deployment and retraction assembly 300 includes a closure plate 376 that is rotationally keyed to pin 372 and positioned within housing 20. Closure plate 376 defines a generally rectangular configuration (although other configurations are also contemplated) and is operably positioned relative to finger 48 of flange 46 of movable handle 40 such that, if movable handle 40 has not been compressed to sufficiently approximate jaw members 110, 120 so as to permit passage of elongated insulative sheath 214 thereabout prior to actuation of deployment and retraction mechanism 300, the rotation of closure plate 376 upon actuation of actuator(s) 380 serves to do so. More specifically, upon actuation of actuator(s) 380 with movable handle 40 disposed in its in initial position or an insufficiently compressed position, closure plate 376 is rotated into contact with finger 48 to urge finger 48 distally, thereby urging movable handle 40 to rotate towards the compressed position to approximate (or further approximate) jaw members 110, 120. Closure plate 376 is oriented about pin 372 such that this approximation (or further approximation) of jaw members 110, 120 is effected prior to advancement of elongated insulative sheath 214 about jaw members 110, 120, thus ensuring that jaw members 110, 120 are sufficiently approximated so as to permit uninhibited advancement of elongated insulative sheath 214 about jaw members 110, 120 to the use position. With respect to retraction, once elongated insulative sheath 214 has cleared jaw members 110, 120, closure plate 376 is rotated out of contact with finger 48, thus permitting movable handle 40 to return to its initial position corresponding to the spaced-apart position of jaw members 110, 120. As noted above, as an alternative to closure plate 376, a cam/slider mechanism operably coupled to pin 372 may be provided for urging movable handle 40 to rotate towards the compressed position to approximate (or further approximate) jaw members 110, 120 upon actuation of actuator(s) 380 with movable handle 40 disposed in its in initial position or an insufficiently compressed position. In such embodiments, rather than having closure plate 376 itself urge movable handle 40 towards the compressed position, the cam washer (not shown), which is rotationally keyed to pin 372, is urged into contact with a cam slider (not shown) which, in turn, is translated into contact with movable handle 40 to urge movable handle 40 to rotate towards the compressed position.

Referring to FIGS. 1, 2, and 28-35, the use and operation of instrument 10 in both the bipolar mode, e.g., for grasping, treating (for example, sealing), and/or cutting tissue, and the monopolar mode, e.g., for electrical/electromechanical tissue treatment, is described. With respect to use in the bipolar mode, monopolar assembly 200 is maintained in the storage condition, wherein elongated insulative sheath 214 is positioned proximally of jaw members 110, 120, distal tissue-treating portion 227 of energizable member 220 is disposed adjacent jaw flanges 114, 124 of jaw members 110, 120, respectively, of end effector assembly 100. In use, instrument 10 is inserted through a cannula, access port, other access device, or directly into a surgical site such that end effector assembly 100 is positioned adjacent tissue to be treated in the bipolar mode of operation. At this point, movable handle 40 may be moved to the initial position such that jaw members 110, 120 are disposed in the spaced-apart position. Further, trigger 62 of trigger assembly 60 remains un-actuated at this point such that knife 164 (FIG. 6) remains disposed in its retracted position.

With jaw members 110, 120 disposed in the spaced-apart position, end effector assembly 100 may be further manipulated into position and/or rotated, e.g., via rotation of rotation wheel 72, such that tissue to be grasped, treated, and/or cut, is disposed between jaw members 110, 120. Next, movable handle 40 is compressed towards fixed handle 50 such that jaw member 110 is pivoted relative to jaw member 120 from the spaced-apart position to the approximated position to grasp tissue therebetween. In this approximated position, and since monopolar assembly 200 is disposed in the storage condition at this point, movable handle 40 may be further compressed, e.g., beyond the point indicated via clicker tab 52 (FIG. 3), such that button activation post 49 depresses depressible button 174 to supply energy to surface 112 of jaw member 110 and/or surface 122 of jaw member 120 for conduction through tissue to treat tissue. Once tissue treatment is complete (or to cut untreated tissue), knife 164 (FIG. 6) may be deployed between jaw members 110, 120, e.g., via actuation of trigger 62 of trigger assembly 60, to cut tissue grasped between jaw members 110, 120.

When tissue cutting is complete, trigger 62 may be released to return knife 164 (FIG. 6) to the retracted position. Thereafter, movable handle 40 may be released or returned to its initial position such that jaw members 110, 120 are moved back to the spaced-apart position to release the treated and/or divided tissue.

For operation of instrument 10 in the monopolar mode, jaw members 110, 120 are first moved to the approximated position, e.g., by compressing movable handle 40 relative to fixed handle 50. However, as detailed above, deployment and retraction mechanism 300 includes a closure feature that operates to urge movable handle 40 towards the compressed position to approximate jaw members 110, 120 upon deployment of monopolar assembly 200, if such has not been done manually prior to deployment. Thus, manual movement of jaw members 110, 120 to the approximated position via compression of movable handle 40 prior to deployment of monopolar assembly 200 need not be performed.

Next, either or both actuators 380 are rotated through a full actuation stroke to deploy monopolar assembly 200 from the storage condition (FIG. 2) to the use condition (FIG. 33), wherein elongated insulative sheath 214 is extended about jaw members 110, 120 and distal tissue-treating portion 227 of energizable member 220 is extended distally from jaw members 110, 120. As can be appreciated, proximal ferrule 212 of monopolar assembly 200, which is fixed relative to housing 20, serves as a buffer between elongated insulative sheath 214 and the cannula, access port, or other access device (not shown), e.g., the instrument seal thereof, and/or between elongated insulative sheath 214 and tissue to reduce friction and inhibit catching of elongated insulative sheath 214 upon deployment and retraction of monopolar assembly 200 and rotation of monopolar assembly 200 relative to housing 20. Upon full actuation, actuator(s) 380 may be released, allowing actuators 380 to return to their initial positions while monopolar assembly 200 is maintained in the use condition. As noted above, if only a partial actuation is effected, monopolar assembly 200 is instead returned with actuators 380 to its previous condition, e.g., the storage condition.

With monopolar assembly 200 disposed in the use condition, either of activation buttons 184 may be depressed to supply energy to distal tissue-treating portion 227 of energizable member 220 to treat tissue therewith. During application of energy to distal tissue-treating portion 227, instrument 10 may be moved relative to tissue, e.g., longitudinally, transversely, and/or radially, to facilitate electromechanical treatment of tissue. At the completion of tissue treatment, either or both of actuators 380 may be actuated through a full actuation a subsequent time to return monopolar assembly 200 to the storage condition.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A deployment and retraction mechanism for selectively deploying and retracting a deployable component of a surgical instrument, the deployment and retraction mechanism comprising:
   a gear box housing a gear assembly;
   a slider operably coupled to an output of the gear assembly, the slider configured to engage the deployable component of the surgical instrument, the slider selectively translatable relative to the gear box between a proximal position, corresponding to a storage condition of the deployable component, and a distal position, corresponding to a use condition of the deployable component; and
   at least one actuator operably coupled to an input of the gear assembly, the at least one actuator movable from an un-actuated position to an actuated position, wherein a full actuation of the at least one actuator is defined as movement of the at least one actuator from the un-actuated position to the actuated position,
   wherein the gear assembly is configured such that:
      upon a full actuation and subsequent release of the at least one actuator, the slider is translated from one of the proximal or distal positions to the other of the proximal or distal positions, and the at least one actuator is returned from the actuated position to the un-actuated position independent of the slider, and
      upon a partial actuation and subsequent release of the at least one actuator, the slider is translated from one of the proximal or distal positions to an intermediate position between the proximal and distal positions and back to the one of the proximal or distal positions, and the at least one actuator is returned from a partially-actuated position between the un-actuated position and the actuated position to the un-actuated position in connection with the translation of the slider back to the one of the proximal or distal position.

2. The deployment and retraction mechanism according to claim 1, wherein the gear box defines a longitudinal slot having a proximal end and a distal end, and wherein the slider is slidable between the proximal end, corresponding to the proximal position of the slider, and the distal end, corresponding to the distal position of the slider.

3. The deployment and retraction mechanism according to claim 2, wherein the slider is operably engaged within a track extending along opposed sides of the longitudinal slot.

4. The deployment and retraction mechanism according to claim 1, wherein the at least one actuator is biased towards the un-actuated position.

5. The deployment and retraction mechanism according to claim 1, wherein the gear assembly includes:
   a ring gear disposed within the gear box and positioned to surround the longitudinal slot; and
   a planet gear coupled to the input of the gear assembly and operably engaged with the ring gear to orbit within the ring gear, the planet gear including an off-center pin rotatably supporting the slider thereon, the planet gear and the ring gear configured such that a one-half orbit of the planet gear within the ring gear translates the slider from one of the proximal or distal positions to the other of the proximal or distal positions.

6. The deployment and retraction mechanism according to claim 5, wherein a full actuation of the at least one actuator urges the planet gear to orbit through a one-half orbit and wherein a partial actuation of the at least one actuator urges the planet gear to orbit less than a one-half orbit.

7. The deployment and retraction mechanism according to claim 5, wherein the gear assembly further includes a carrier member defining an off-center pivot, the off-center pivot of the carrier member received within a central aperture defined within the planet gear to operably couple the planet gear and the carrier member such that rotation of the carrier member orbits the planet gear within the ring gear.

8. The deployment and retraction mechanism according to claim 7, wherein the gear assembly further includes a ratchet gear releasably engagable with the carrier member.

9. The deployment and retraction mechanism according to claim 8, wherein the at least one actuator is operably coupled to the ratchet gear such that actuation of the at least one actuator effects rotation of the ratchet gear to thereby rotate the carrier member when the ratchet gear is engaged with the carrier member.

10. The deployment and retraction mechanism according to claim 9, wherein the gear assembly further includes a disengagement plate disposed between the ratchet gear and the carrier member, the disengagement plate configured to selectively disengage the ratchet gear from the carrier member upon a full actuation of the at least one actuator.

11. The deployment and retraction mechanism according to claim 10, wherein the ratchet gear remains engaged with the carrier member upon a partial actuation of the at least one actuator.

12. A surgical instrument, comprising:
a housing having a shaft extending distally therefrom;
an end effector assembly disposed at a distal end of the shaft;
a deployable assembly selectively movable relative to the end effector assembly between a storage condition and a use condition; and
a deployment and retraction mechanism for selectively deploying and retracting the deployable assembly, the deployment and retraction mechanism including:
a gear box mounted within the housing and operably retaining a gear assembly therein;
a slider operably coupled to the gear assembly and the deployable assembly, the slider selectively translatable relative to the gear box between a proximal position, corresponding to the storage condition of the deployable assembly, and a distal position, corresponding to the use condition of the deployable assembly; and
at least one actuator disposed on the housing and operably coupled to the gear assembly, the at least one actuator movable relative to the housing from an un-actuated position to an actuated position, wherein a full actuation of the at least one actuator is defined as movement of the at least one actuator from the un-actuated position to the actuated position,
wherein the gear assembly is configured such that:
upon a full actuation and subsequent release of the at least one actuator, the slider is translated from one of the proximal or distal positions to the other of the proximal or distal positions, and the at least one actuator is returned from the actuated position to the un-actuated position independent of the slider, and upon a partial actuation and subsequent release of the at least one actuator, the slider is translated from one of the proximal or distal positions to an intermediate position between the proximal and distal positions and back to the one of the proximal or distal positions, and the at least one actuator is returned from a partially-actuated position between the un-actuated position and the actuated position to the un-actuated position in connection with the translation of the slider back to the one of the proximal or distal positions.

13. The surgical instrument according to claim 12, wherein the deployable assembly includes:
an elongated insulative sheath slidably disposed about the shaft; and
an energizable member slidably disposed within the shaft.

14. The surgical instrument according to claim 13, wherein, in the storage condition, the elongated insulative sheath and the energizable member are positioned proximally of the end effector assembly, and wherein, in the use condition, the elongated insulative sheath extends about the end effector assembly and the energizable member extends distally from the end effector assembly.

15. The surgical instrument according to claim 12, wherein the gear assembly includes:
a ring gear disposed within the gear box; and
a planet gear operably engaged with the ring gear to orbit within the ring gear, the planet gear including an off-center pin rotatably supporting the slider thereon, the planet gear and the ring gear configured such that a one-half orbit of the planet gear within the ring gear translates the slider from one of the proximal or distal positions to the other of the proximal or distal positions.

16. The surgical instrument according to claim 15, wherein the gear assembly further includes a carrier member defining an off-center pivot, the off-center pivot of the carrier member received within a central aperture of the planet gear to operably couple the planet gear and the carrier member such that rotation of the carrier member orbits the planet gear within the ring gear.

17. The surgical instrument according to claim 16, wherein the gear assembly further includes a disengagement plate operably coupled between the at least one actuator and the carrier member, the disengagement plate configured to selectively disengage the at least one actuator from the carrier member upon a full actuation of the at least one actuator to permit the at least one actuator to return from the actuated position to the un-actuated position independent of the slider.

18. The surgical instrument according to claim 17, wherein the at least one actuator remains engaged with the carrier member upon a partial actuation of the at least one actuator such that the slider is translated back to the one of the proximal or distal positions upon return of the at least one actuator from a partially-actuated position between the un-actuated position and the actuated position to the un-actuated position.

19. The surgical instrument according to claim 12, wherein the at least one actuator is biased towards the un-actuated position.

20. The surgical instrument according to claim 12, wherein the slider is translatable along a track defined within the gear box.

* * * * *